(12) United States Patent
Rabinow et al.

(10) Patent No.: US 8,263,131 B2
(45) Date of Patent: Sep. 11, 2012

(54) METHOD FOR TREATING INFECTIOUS ORGANISMS NORMALLY CONSIDERED TO BE RESISTANT TO AN ANTIMICROBIAL DRUG

(75) Inventors: Barrett Rabinow, Skokie, IL (US); Randy White, Woodbury, MN (US); Chong-Son Sun, Lake Forest, IL (US); Joseph Chung Take Wong, Gurnee, IL (US); James E. Kipp, Wauconda, IL (US); Mark Doty, Grayslake, IL (US); Christine L. Rebbeck, Algonquin, IL (US); Pavlos Papadopoulos, Antioch, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 485 days.

(21) Appl. No.: 12/414,484

(22) Filed: Mar. 30, 2009

(65) Prior Publication Data
US 2010/0086611 A1  Apr. 8, 2010

Related U.S. Application Data

(60) Division of application No. 10/834,541, filed on Apr. 29, 2004, now abandoned, which is a continuation-in-part of application No. 10/270,268, filed on Oct. 11, 2002, now abandoned, which is a continuation-in-part of application No. 10/021,692, filed on Dec. 12, 2001, now Pat. No. 6,884,436, which is a continuation-in-part of application No. 09/953,979, filed on Sep. 17, 2001, now Pat. No.

(Continued)

(51) Int. Cl.
*A61K 9/14* (2006.01)
(52) U.S. Cl. .................................................... 424/489
(58) Field of Classification Search .................... None
See application file for complete search history.

(56) References Cited

U.S. PATENT DOCUMENTS
2,745,785 A   5/1956   Bruce et al.
(Continued)

FOREIGN PATENT DOCUMENTS
EP   0169618   1/1986
(Continued)

OTHER PUBLICATIONS

Martin, The use of fluconazole and itraconazole in the treatment of *Candida albicans* infections, Journal of Antimicrobial Chemotherapy, 1999, 44, 429-437.*

(Continued)

*Primary Examiner* — Paul Dickinson
(74) *Attorney, Agent, or Firm* — Marshall, Gerstein & Borun LLP

(57) ABSTRACT

The present invention relates to compositions of submicron-to micron-size particles of antimicrobial agents. More particularly the invention relates to a composition of an antimicrobial agent that renders the agent potent against organisms normally considered to be resistant to the agent. The composition comprises an aqueous suspension of submicron- to micron-size particles containing the agent coated with at least one surfactant selected from the group consisting of: ionic surfactants, non-ionic surfactants, biologically derived surfactants, and amino acids and their derivatives. The particles have a volume-weighted mean particle size of less than 5 μm as measured by laser diffractometry.

10 Claims, 10 Drawing Sheets

Related U.S. Application Data 6,951,656, which is a continuation-in-part of application No. 09/874,637, filed on Jun. 5, 2001, now Pat. No. 6,869,617, said application No. 10/021,692 is a continuation-in-part of application No. 10/035,821, filed on Oct. 19, 2001, now Pat. No. 6,977,085, which is a continuation-in-part of application No. 09/953,979, said application No. 10/270,268 is a continuation-in-part of application No. 10/246,802, filed on Sep. 17, 2002, now abandoned, which is a continuation-in-part of application No. 10/035,821.

(60) Provisional application No. 60/466,354, filed on Apr. 29, 2003, provisional application No. 60/258,160, filed on Dec. 22, 2000.

(56) References Cited

U.S. PATENT DOCUMENTS

| | | |
|---|---|---|
| 3,685,261 A | 8/1972 | McIlvaine et al. |
| 4,056,635 A | 11/1977 | Glen et al. |
| 4,073,943 A | 2/1978 | Wretlind et al. |
| 4,340,589 A | 7/1982 | Uemura et al. |
| 4,452,817 A | 6/1984 | Glen et al. |
| 4,540,602 A | 9/1985 | Motoyama et al. |
| 4,606,670 A | 8/1986 | Angell |
| 4,606,940 A | 8/1986 | Frank et al. |
| 4,608,278 A | 8/1986 | Frank et al. |
| 4,622,219 A | 11/1986 | Haynes |
| 4,725,442 A | 2/1988 | Haynes |
| 4,786,735 A | 11/1988 | Graboyes et al. |
| 4,798,846 A | 1/1989 | Glen et al. |
| 4,826,689 A | 5/1989 | Violanto |
| 4,973,465 A | 11/1990 | Baurain et al. |
| 4,997,454 A | 3/1991 | Violante et al. |
| 5,023,271 A | 6/1991 | Vigne et al. |
| 5,049,322 A | 9/1991 | Devissaguet et al. |
| 5,078,994 A | 1/1992 | Nair et al. |
| 5,091,187 A | 2/1992 | Haynes |
| 5,091,188 A | 2/1992 | Haynes |
| 5,100,591 A | 3/1992 | Leclef et al. |
| 5,118,528 A | 6/1992 | Fessi et al. |
| 5,122,543 A | 6/1992 | Khanna |
| 5,133,908 A | 7/1992 | Stainmesse et al. |
| 5,145,684 A | 9/1992 | Liversidge et al. |
| 5,151,264 A | 9/1992 | Samain et al. |
| 5,152,923 A | 10/1992 | Weder et al. |
| 5,171,566 A | 12/1992 | Mizushima et al. |
| 5,174,930 A | 12/1992 | Stainmesse et al. |
| 5,188,837 A | 2/1993 | Domb |
| 5,235,073 A * | 8/1993 | Kim et al. ..................... 549/408 |
| 5,246,707 A | 9/1993 | Haynes |
| 5,250,236 A | 10/1993 | Gasco |
| 5,269,979 A | 12/1993 | Fountain |
| 5,298,262 A | 3/1994 | Na et al. |
| 5,302,401 A | 4/1994 | Liversidge et al. |
| 5,306,519 A | 4/1994 | Peterson et al. |
| 5,314,506 A | 5/1994 | Midler, Jr. et al. |
| 5,318,767 A | 6/1994 | Liversidge et al. |
| 5,326,552 A | 7/1994 | Na et al. |
| 5,336,507 A | 8/1994 | Na et al. |
| 5,340,564 A | 8/1994 | Illig et al. |
| 5,346,702 A | 9/1994 | Na et al. |
| 5,347,006 A | 9/1994 | Lavacchielli et al. |
| 5,352,459 A | 10/1994 | Hollister et al. |
| 5,354,563 A | 10/1994 | Toyotama |
| 5,389,263 A | 2/1995 | Gallagher et al. |
| 5,399,363 A | 3/1995 | Liversidge et al. |
| 5,417,956 A | 5/1995 | Moser |
| 5,429,824 A | 7/1995 | June |
| 5,447,710 A | 9/1995 | Na et al. |
| 5,466,646 A | 11/1995 | Moser |
| 5,470,583 A | 11/1995 | Na et al. |
| 5,474,989 A | 12/1995 | Hashimoto et al. |
| 5,494,683 A | 2/1996 | Liversidge et al. |
| 5,510,118 A | 4/1996 | Bosch et al. |
| 5,518,187 A | 5/1996 | Bruno et al. |
| 5,518,738 A | 5/1996 | Eickhoff et al. |
| 5,534,270 A | 7/1996 | De Castro |
| 5,543,133 A | 8/1996 | Swanson et al. |
| RE35,338 E | 9/1996 | Haynes |
| 5,552,160 A | 9/1996 | Liversidge et al. |
| 5,560,932 A | 10/1996 | Bagchi et al. |
| 5,560,933 A | 10/1996 | Soon-Shiong et al. |
| 5,565,383 A | 10/1996 | Sakai |
| 5,569,448 A | 10/1996 | Wong et al. |
| 5,573,783 A | 11/1996 | Desieno et al. |
| 5,578,325 A | 11/1996 | Domb et al. |
| 5,580,579 A | 12/1996 | Ruddy et al. |
| 5,587,143 A | 12/1996 | Wong |
| 5,591,456 A | 1/1997 | Franson et al. |
| 5,605,785 A | 2/1997 | Texter et al. |
| 5,626,864 A | 5/1997 | Rosenberg et al. |
| 5,635,609 A | 6/1997 | Levy et al. |
| 5,641,515 A | 6/1997 | Ramtoola |
| 5,641,745 A | 6/1997 | Ramtoola |
| 5,660,858 A | 8/1997 | Parikh et al. |
| 5,662,883 A | 9/1997 | Bagchi et al. |
| 5,662,932 A | 9/1997 | Amselem et al. |
| 5,663,198 A * | 9/1997 | Reul et al. ..................... 514/471 |
| 5,665,331 A | 9/1997 | Bagchi et al. |
| 5,665,383 A | 9/1997 | Grinstaff et al. |
| 5,679,576 A | 10/1997 | Kawai et al. |
| 5,707,634 A | 1/1998 | Schmitt |
| 5,716,642 A | 2/1998 | Bagchi et al. |
| 5,720,551 A | 2/1998 | Shechter |
| 5,766,635 A | 6/1998 | Spenleuhauer et al. |
| 5,780,062 A | 7/1998 | Frank et al. |
| 5,833,891 A | 11/1998 | Subramaniam et al. |
| 5,858,410 A | 1/1999 | Muller et al. |
| 5,862,999 A | 1/1999 | Czekai et al. |
| 5,874,111 A | 2/1999 | Maitra et al. |
| 5,874,574 A | 2/1999 | Johnston et al. |
| 5,916,583 A | 6/1999 | Broberg et al. |
| 5,916,596 A | 6/1999 | Desai et al. |
| 5,922,355 A | 7/1999 | Parikh et al. |
| 5,939,100 A | 8/1999 | Albrechtsen et al. |
| 5,968,251 A | 10/1999 | Auweter et al. |
| 5,981,719 A | 11/1999 | Woiszwillo et al. |
| 5,989,583 A | 11/1999 | Amselem et al. |
| 6,007,845 A | 12/1999 | Domb et al. |
| 6,039,981 A | 3/2000 | Woo et al. |
| 6,045,826 A | 4/2000 | Borowy-Borowski et al. |
| 6,045,829 A | 4/2000 | Liversidge et al. |
| 6,048,550 A | 4/2000 | Chan et al. |
| 6,063,138 A | 5/2000 | Hanna et al. |
| 6,063,910 A | 5/2000 | Debenedetti et al. |
| 6,068,858 A | 5/2000 | Liversidge et al. |
| 6,086,376 A | 7/2000 | Moussa et al. |
| 6,090,925 A | 7/2000 | Woiszwillo et al. |
| 6,090,983 A | 7/2000 | Yokoyama et al. |
| 6,132,750 A | 10/2000 | Perrier et al. |
| 6,139,870 A | 10/2000 | Verrecchia et al. |
| 6,143,211 A | 11/2000 | Mathiowitz et al. |
| 6,143,778 A | 11/2000 | Gautier et al. |
| 6,146,663 A | 11/2000 | Bissery et al. |
| 6,153,219 A | 11/2000 | Creeth et al. |
| 6,153,225 A | 11/2000 | Lee et al. |
| 6,165,506 A | 12/2000 | Jain et al. |
| 6,177,103 B1 | 1/2001 | Pace et al. |
| 6,197,757 B1 | 3/2001 | Perrier et al. |
| 6,207,134 B1 | 3/2001 | Fahlvik et al. |
| 6,207,178 B1 | 3/2001 | Westesen et al. |
| 6,214,384 B1 | 4/2001 | Pallado et al. |
| 6,217,886 B1 | 4/2001 | Onyuksel et al. |
| 6,221,332 B1 | 4/2001 | Thumm et al. |
| 6,221,398 B1 | 4/2001 | Jakupovic et al. |
| 6,221,400 B1 | 4/2001 | Liversidge et al. |
| 6,228,399 B1 | 5/2001 | Parikh et al. |
| 6,231,890 B1 | 5/2001 | Naito et al. |
| 6,235,224 B1 | 5/2001 | Mathiowitz et al. |
| 6,238,677 B1 | 5/2001 | Fanta et al. |
| 6,238,694 B1 | 5/2001 | Gasco et al. |
| 6,245,349 B1 | 6/2001 | Yiv et al. |

| | | | | | | |
|---|---|---|---|---|---|---|
| 6,248,363 | B1 | 6/2001 | Patel et al. | EP | 0752245 | 1/1997 |
| 6,264,922 | B1 | 7/2001 | Wood et al. | EP | 0754034 | 1/1997 |
| 6,267,989 | B1 | 7/2001 | Liversidge et al. | EP | 0788350 | 8/1997 |
| 6,268,053 | B1 | 7/2001 | Woiszwillo et al. | EP | 0804162 | 11/1997 |
| 6,270,806 | B1 | 8/2001 | Liversidge et al. | EP | 0808154 | 11/1997 |
| 6,294,204 | B1 | 9/2001 | Rossling et al. | EP | 0812187 | 12/1997 |
| 6,299,906 | B1 | 10/2001 | Bausch et al. | EP | 0820300 | 1/1998 |
| 6,306,406 | B1 | 10/2001 | Deluca | EP | 0828479 | 3/1998 |
| 6,337,092 | B1 | 1/2002 | Khan et al. | EP | 0831770 | 4/1998 |
| 6,344,271 | B1 | 2/2002 | Yadav et al. | EP | 0832569 | 4/1998 |
| 6,346,533 | B1 | 2/2002 | Cha et al. | EP | 0988863 | 3/2000 |
| 6,365,191 | B1 | 4/2002 | Burman et al. | EP | 1012204 | 6/2000 |
| 6,375,986 | B1 | 4/2002 | Ryde et al. | EP | 1023050 | 8/2000 |
| 6,395,300 | B1 | 5/2002 | Straub et al. | EP | 1044683 | 10/2000 |
| 6,428,814 | B1 | 8/2002 | Bosch et al. | EP | 1105109 | 6/2001 |
| 6,458,387 | B1 | 10/2002 | Scott et al. | EP | 1156788 | 11/2001 |
| 6,462,093 | B1 | 10/2002 | Miyamoto et al. | EP | 1210942 | 6/2002 |
| 6,469,786 | B2 | 10/2002 | Shimaoka | EP | 1269994 | 1/2003 |
| 6,509,038 | B2 | 1/2003 | Baert et al. | EP | 1347747 | 10/2003 |
| 6,607,784 | B2 | 8/2003 | Kipp et al. | FR | 2817478 | 6/2002 |
| 6,610,317 | B2 | 8/2003 | Straub et al. | JP | 02306902 | 12/1990 |
| 6,616,869 | B2 | 9/2003 | Mathiowitz et al. | WO | WO-85/00011 | 1/1985 |
| 6,632,443 | B2 | 10/2003 | Borowy-Borowski et al. | WO | WO-86/03676 | 7/1986 |
| 6,632,671 | B2 | 10/2003 | Unger | WO | WO-89/11850 | 12/1989 |
| 6,635,223 | B2 | 10/2003 | Maerz | WO | WO-90/03782 | 4/1990 |
| 6,667,048 | B1 | 12/2003 | Lambert et al. | WO | WO-90-15593 | 12/1990 |
| 6,669,961 | B2 | 12/2003 | Kim et al. | WO | WO-91/06292 | 5/1991 |
| 6,682,761 | B2 | 1/2004 | Pace et al. | WO | WO-91-07170 | 5/1991 |
| 6,696,019 | B2 | 2/2004 | Laugharn, Jr. et al. | WO | WO-91/12794 | 9/1991 |
| 6,835,396 | B2 | 12/2004 | Brynjelsen et al. | WO | WO-91-16068 | 10/1991 |
| 6,869,617 | B2 | 3/2005 | Kipp et al. | WO | WO-92/00731 | 1/1992 |
| 6,884,436 | B2 | 4/2005 | Kipp et al. | WO | WO-92/03380 | 3/1992 |
| 6,951,656 | B2 | 10/2005 | Kipp et al. | WO | WO-92/17214 | 10/1992 |
| 6,977,085 | B2 | 12/2005 | Werling et al. | WO | WO-93/25190 | 12/1993 |
| 7,037,528 | B2 | 5/2006 | Kipp et al. | WO | WO-94/07999 | 4/1994 |
| 7,105,176 | B2 | 9/2006 | Auweter et al. | WO | WO-94/20072 | 9/1994 |
| 7,112,340 | B2 | 9/2006 | Kipp et al. | WO | WO-95/05164 | 2/1995 |
| 7,193,084 | B2 | 3/2007 | Werling et al. | WO | WO-95/27482 | 10/1995 |
| 7,338,657 | B2 | 3/2008 | Vogel et al. | WO | WO-95/33488 | 12/1995 |
| 7,374,779 | B2 | 5/2008 | Chen et al. | WO | WO-96/00567 | 1/1996 |
| 7,374,782 | B2 | 5/2008 | Brown | WO | WO-96/14833 | 5/1996 |
| 2002/0012675 | A1 | 1/2002 | Jain et al. | WO | WO-96/20698 | 7/1996 |
| 2002/0048610 | A1 | 4/2002 | Cima et al. | WO | WO-96/24336 | 8/1996 |
| 2003/0054042 | A1 | 3/2003 | Liversidge et al. | WO | WO-96/24340 | 8/1996 |
| 2003/0072807 | A1 | 4/2003 | Wong et al. | WO | WO 96/25150 | 8/1996 |
| 2003/0077297 | A1* | 4/2003 | Chen et al. ............... 424/400 | WO | WO-96/25152 | 8/1996 |
| 2003/0096013 | A1 | 5/2003 | Werling et al. | WO | WO-96/25918 | 8/1996 |
| 2003/0170279 | A1 | 9/2003 | Lambert et al. | WO | WO-96/31231 | 10/1996 |
| 2003/0206959 | A9 | 11/2003 | Kipp et al. | WO | WO 97/03651 | 2/1997 |
| 2004/0022861 | A1 | 2/2004 | Williams | WO | WO 97/03657 | 2/1997 |
| 2004/0022862 | A1 | 2/2004 | Kipp et al. | WO | WO-97/14407 | 4/1997 |
| 2004/0245662 | A1 | 12/2004 | Chaubal et al. | WO | WO-97/30695 | 8/1997 |
| 2004/0256749 | A1 | 12/2004 | Chaubal et al. | WO | WO-97/36611 | 10/1997 |
| 2005/0013868 | A1 | 1/2005 | Brynjelsen et al. | WO | WO-97/41837 | 11/1997 |
| 2005/0037083 | A1 | 2/2005 | Brynjelsen et al. | WO | WO-97/44014 | 11/1997 |
| 2005/0244503 | A1 | 11/2005 | Rabinow et al. | WO | WO-98/01162 | 1/1998 |
| | | | | WO | WO-98/07410 | 2/1998 |
| | | FOREIGN PATENT DOCUMENTS | | WO | WO-98/07414 | 2/1998 |
| | | | | WO | WO-98/14170 | 4/1998 |
| EP | | 0207134 | 1/1987 | WO | WO-98/14174 | 4/1998 |
| EP | | 0275796 | 7/1988 | WO | WO-98/14180 | 4/1998 |
| EP | | 0349428 | 1/1990 | WO | WO-98/24450 | 6/1998 |
| EP | | 0372070 | 6/1990 | WO | WO-98/31346 | 7/1998 |
| EP | | 0377477 | 7/1990 | WO | WO-98/35666 | 8/1998 |
| EP | | 0379379 | 7/1990 | WO | WO-98/47492 | 10/1998 |
| EP | | 0423697 | 4/1991 | WO | WO-98/57967 | 12/1998 |
| EP | | 0498482 | 8/1992 | WO | WO-99/00113 | 1/1999 |
| EP | | 0499299 | 8/1992 | WO | WO-99/02665 | 1/1999 |
| EP | | 0517565 | 12/1992 | WO | WO-99/03450 | 1/1999 |
| EP | | 0535534 | 4/1993 | WO | WO-99/16443 | 4/1999 |
| EP | | 0577215 | 1/1994 | WO | WO-99/29316 | 6/1999 |
| EP | | 0600532 | 6/1994 | WO | WO-99/30833 | 6/1999 |
| EP | | 0601618 | 6/1994 | WO | WO-99/32156 | 7/1999 |
| EP | | 0601619 | 6/1994 | WO | WO-99/33467 | 7/1999 |
| EP | | 0602700 | 6/1994 | WO | WO-99/38493 | 8/1999 |
| EP | | 0602702 | 6/1994 | WO | WO-99/39700 | 8/1999 |
| EP | | 0605024 | 7/1994 | WO | WO-99/49846 | 10/1999 |
| EP | | 0644755 | 3/1995 | WO | WO-99/49848 | 10/1999 |
| EP | | 0720471 | 7/1996 | WO | WO-99/59550 | 11/1999 |
| EP | | 0730406 | 9/1996 | | | |

| | | |
|---|---|---|
| WO | WO-99/61001 | 12/1999 |
| WO | WO-99/65469 | 12/1999 |
| WO | WO-00/03697 | 1/2000 |
| WO | WO-00/06152 | 2/2000 |
| WO | WO-00/09096 | 2/2000 |
| WO | WO-00/12124 | 3/2000 |
| WO | WO-00/12125 | 3/2000 |
| WO | WO-00/18374 | 4/2000 |
| WO | WO-00/27363 | 5/2000 |
| WO | WO-00/30615 | 6/2000 |
| WO | WO-00/30616 | 6/2000 |
| WO | WO-00/37050 | 6/2000 |
| WO | WO-00/38811 | 7/2000 |
| WO | WO-00/40220 | 7/2000 |
| WO | WO-00/51572 | 9/2000 |
| WO | WO-00/56726 | 9/2000 |
| WO | WO-00/71079 | 11/2000 |
| WO | WO-01/12155 | 2/2001 |
| WO | WO-01/17546 | 3/2001 |
| WO | WO-01/21154 | 3/2001 |
| WO | WO-01/26635 | 4/2001 |
| WO | WO-01/62374 | 8/2001 |
| WO | WO-01/64164 | 9/2001 |
| WO | WO-01/80828 | 11/2001 |
| WO | WO-01/85345 | 11/2001 |
| WO | WO-01/87264 | 11/2001 |
| WO | WO-02/17883 | 3/2002 |
| WO | WO-02/24163 | 3/2002 |
| WO | WO-02/24169 | 3/2002 |
| WO | WO-02/43702 | 6/2002 |
| WO | WO-02/051386 | 7/2002 |
| WO | WO-02/055059 | 7/2002 |
| WO | WO-02/060411 | 8/2002 |
| WO | WO-02/072070 | 9/2002 |
| WO | WO-02/072071 | 9/2002 |
| WO | WO-02/074282 | 9/2002 |
| WO | WO-02/076446 | 10/2002 |
| WO | WO-02/080678 | 10/2002 |
| WO | WO-02/080883 | 10/2002 |
| WO | WO-02/082074 | 10/2002 |
| WO | WO-02/089773 | 11/2002 |
| WO | WO-03/024424 | 3/2003 |
| WO | WO-03/026611 | 4/2003 |
| WO | WO-03/035031 | 5/2003 |
| WO | WO-03/045330 | 6/2003 |
| WO | WO-03/045660 | 6/2003 |
| WO | WO-2004/082659 | 9/2004 |
| WO | WO-2004/103348 | 12/2004 |
| WO | WO-2004/112747 | 12/2004 |

OTHER PUBLICATIONS http://www.who.int/mediacentre/factsheets/fs194/en/, accessed May 20, 2011.*

Allen et al., "Critical evaluation of acute cardiopulmonary toxicity of microspheres," *J. Nucl. Med.*, 19:1204-8 (1987).

Allen et al., "Effects on the murine mononuclear phagocyte system of chronic administration of liposomes containing cytotoxic drug or lipid A compared with empty liposomes," *Can. J. Physiol. Pharmacol.*, 65:185-90 (1987).

Allen et al., "Large unilamellar liposomes with low uptake into the reticuloendothelial system," *FEBS Lett.*, 223:42-46 1987.

Anonymous, Crystal growing, retrieved from the Internet: URL:http://www.chem.tamu.edu/xray/pdf/guide%20to%20crystal%20growth.pdf >, 2009.

Aquaro et al., "Macrophages and HIV infection: therapeutical approaches toward this strategic virus reservoir," *Antiviral Res.*, 55:209-25 (2002).

Avanti Polar Lipids, Inc., "Polymer and polymerizable lipids: polyethylene glycol)-lipid conjugates," (Mar. 2003), retrieved from the Internet: <URL: http://www.avantilipids.com>.

Avanti Polar Lipids, Inc., "Polymer and polymerizable lipids: functionalized PEG lipids," (Mar. 2003), retrieved from the Internet: <URL: http://www.avantilipids.com>.

Avanti Polar Lipids, Inc., "Synthetic products—functionalized phospholipids: lipids for conjugation of proteins/pepetides/drugs to lipsomes," (Mar. 2003), retrieved from the Internet: <URL: http://www.avantilipids.com>.

Bacher et al., "D-24851, a novel synthetic microtubule inhibitor, exerts curative antitumoral activity in vivo, shows efficacy toward multidrug-resistant tumor cells, and lacks neurotoxicity," *Cancer Res.*, 61: 392-9 (2001).

Bender et al., "Efficiency of nanoparticles as a carrier for antiviral agents in human immunodeficiency virus-infected human monocytes/macrophases in vitro, antimicrobial agents and chemotherapy," *Antimicrob. Agents Chemother.*, 40:1467-71 (1996).

Broxterman et al., "Cancer research 2001: Drug resistance, new targets and drug combinations" *Drug Resistance Updates*, 4:197-209 (2001).

Crowe et al., "The contribution of monocyte infection and trafficking to viral persistence, and maintenance of the viral reservoir in HIV infection," *J. Leukoc. Biol.*, 74:635-641 (2003).

Davis et al., "Pulmonary perfusion imaging: acute toxicity and safety factors as a function of particle size," *J. Nucl. Med.*, 19:1209-1213 (1978).

Duncker et al., "Effects of the pharmaceutical cosolvent hydroxypropyl-beta-cyclodextrin on porcine corneal endothelium," *Graefes Arch. Clin. Exp. Opthalmol.*, 236::380-9 (1998).

Eugen Müller (ed.), Methoden der Organischen Chemie—Allgemeine Laboratoriumspraxis, 1958, Georg Thieme Verlag, Stuttgart, p. 375.

Fischer-Smith et al., "CNS invasion by CD14+/CD16+ peripheral blood-derived monocytes in HIV dementia: perivascular accumulation and reservoir of HIV infection," *J. Neurovirol.*, 7:528-41 (2001).

Graham et al., "The effects of freezing on commercial insulin suspensions," *Int. J. Pharmaceutics*, (1978).

Gurinder et al., "Analysis of systems failure leading to medication errors: The role of sentinel events for anesthesiologists," Anesthesiology Abstracts of Scientific Papers Annual Meeting, No. 2002, Abstract No. A-1153 (2002).

Heiati et al., "Solid lipid nanoparticles as drug carriers: II. Plasma stability and biodistribution of solid lipid nanoparticles containing the lipophilic prodrug 3" -azido-3" -deoxythymidine palmitate in mice," *Int. J. Pharmaceutics*, 174:71-80 (1998).

Igarashi et al., "Macrophage are the principal reservoir and sustain high virus loads in rhesus macaques after the depletion of CD4+ T cells by a highly pathogenic simian immunodeficiency virus/HIV type 1 chimera (SHIV): implications for HIV-1 infections of humans," *Proc. Natl. Acad. Sci. USA*, 98:658-63 (2001).

Kinman et al., "Lipid-drug association enhanced HIV-1 protease inhibitor indinavir localize ion in lymphoid tissues and viral load reduction: a proof of concept study in HIV-2287-infected macaques," *J. Acquir. Immune Defic. Syndr.*, 34:387-97 (2003).

Lavelle et al., "American Association for Cancer Research 1999: Apr. 10-14, Philadelphia, Pennsylvania," Exp. Opin. Investigations Drugs, 8:903-9 (1999).

Limoges et al., "Sustained antiretroviral activity of indinavir nanosuspensions in primary monocyte-derived macrophages," poster presentation, 11th Conference on Retroviruses and Opportunistic Infections, Feb. 8-11, 2004.

Lobenberg et al., "Body distribution of azidothymidine bound to hexyl-cyanoacrylate nanoparticles after i.v. injection to rats," *J. Control. Release*, 50:21-30 (1998).

Lobenberg et al., "Macrophage targeting of azidothymidine: a promising strategy for AIDS therapy," *AIDS Res. Hum. Retroviruses*, 12:1709-15 (1996).

Meyer et al., "High-pressure sterilization of foods," *Food Technology*, 54:67-72 (Nov. 2000).

Moghimi et al., "Long-circulating and target-specific nanoparticles: theory to practice," *Pharmacol. Rev.*, 53:283-318 (2001).

Mroczka, "Integral transform technique in particle sizing," *J. Aerosol Sci.*, 20:1075-7 (1989).

Na et al., "Cloud point of nonionic surfactants: modulation with pharmaceutical excipients," *Pharmaceutical Research*, 16:562-8 (1999).

Nesbit et al., "In vitro and animal models of human immunodeficiency virus infection of the central nervous system," *Clin. Diagn. Lab. Immunol.*, 9:515-24 (2002).

Nottet et al., "HIV-1 entry into brain: Mechanisms for the infiltration of HIV-1-infected macrophages across the blood-brain barrier," p.

55, in Gendelman (ed.) et al., *The Neurology of AIDS*, New York: Hodder Arnold Publication (1997).

Perno et al., "Relative potency of protease inhibitors in monocytes/macrophages acutely and chronically infected with human immunodeficiency virus," *J. Infect. Dis.*, 178:413-22 (1998).

Rabinow, "Nanosuspensions in drug delivery," *Nat. Rev. Drug Discov.*, 3:785-96 (2004).

Ricketts, Project Habbakuk, Retrieved from the Internet on Aug. 20, 2007, <URL: http:www.mysteriesofcanada.com/Alberta/habbakuk.htm>.

Sawchuk et al., "Investigation of distribution, transport and uptake of anti-HIV drugs to the central nervous system," *Adv. Drug Deliv. Rev.*, 39:5-31 (1999).

Schroeder et al., "Distribution of radiolabeled subvisible microspheres after intravenous administration to beagle dogs," *J. Pharm. Sci.*, 67:504-7 (1978).

Schroeder et al., "Physiological effects of subvisible microspheres administered intravenously to beagle dogs," *J. Pharm. Sci.*, 67:508-13 (1978).

Shrayer et al., Ceramide, a mediator of apoptosis, synergizes with paclitaxel to induce regression of the L3.6 human pancreatic carcinoma implanted in SCID mice, *J. Clin. Oncol.*, 22:2135 (2004).

Singla et al., "Paclitaxel and its formulations," *Int. J. Pharm.*, 235:179-192 (2002).

Sjostrom et al., "A method for the preparation of submicron particles of sparingly water-soluble drugs by precipitation in oil-in-water emulsions. II: Influence of the emulsifier, the solvent, and the drug substance," *J. Pharm. Sci.*, 82:584-9 (1993).

Sjostrom et al., "Preparation of submicron drug particles in lecithin-stabilized o/w emulsions I. Model studies of the precipitation of cholesteryl acetate," *Int. J. Pharm.*, 88:53-62 (1992).

Sjostrom et al., "The formation of submicron organic particles by precipitation in an emulsion," *J. Dispers. Sci. Tech.*, 15:89-117 (1994).

Solas et al., "Discrepancies between protease inhibitor concentrations and viral load in reservoirs and sanctuary sites in human immunodeficiency virus-infected patients," *Antimicrob. Agents Chemother.*, 47:238-43 (2003).

Subramaniam et al., "Pharmaceutical processing with supercritical carbon dioxide," *J. Pharm. Sci.*, 86:885-90 (1997).

Volcheck et al., "Anaphylaxis to intravenous cyclosporine and tolerance to oral cyclosporine: case resort and review," *Ann. Allergy Asthma Immunol.*, 80:159-63 (1998).

Von Briesen et al., "Controlled release of antiretroviral drugs," *AIDS Rev.*, 2:31-8 (2000).

Yokel et al., "Acute toxicity of latex microspheres," *Toxicol. Lett.*, 9:165-70 (1981).

\* cited by examiner

METHOD FOR TREATING INFECTIOUS ORGANISMS NORMALLY CONSIDERED TO BE RESISTANT TO AN ANTIMICROBIAL DRUG

CROSS REFERENCE TO RELATED APPLICATIONS

This is a divisional application of U.S. patent application Ser. No. 10/834,541, filed Apr. 29, 2004, which claims priority from provisional application Ser. No. 60/466,354, filed on Apr. 29, 2003, and which is also a continuation-in-part of U.S. application Ser. No. 10/270,268, filed on Oct. 11, 2002, which is a continuation-in-part of U.S. patent application Ser. No. 10/246,802 filed Sep. 17, 2002, which is a continuation-in-part of U.S. patent application Ser. No. 10/035,821 filed Oct. 19, 2001, all of which are incorporated herein by reference and made a part hereof. U.S. patent application Ser. No. 10/270,268, filed on Oct. 11, 2002, is also a continuation-in-part of U.S. patent application Ser. No. 10/021,692 filed Dec. 12, 2001, which is incorporated herein by reference and made a part hereof. Both U.S. patent application Ser. No. 10/035,821 filed Oct. 19, 2001 and U.S. patent application Ser. No. 10/021,692 filed Dec. 12, 2001 are continuations-in-part of U.S. patent application Ser. No. 09/953,979 filed Sep. 17, 2001, which is a continuation-in-part of U.S. patent application Ser. No. 09/874,637 filed Jun. 5, 2001, which claims priority from provisional Application Ser. No. 60/258,160 filed Dec. 22, 2000, all of which are incorporated herein by reference and made apart hereof. U.S. patent application Ser. No. 10/021,692, filed on Dec. 12, 2001, is also a continuation-in-part of U.S. patent application Ser. No. 10/035,821, filed on Oct. 19, 2001.

FEDERALLY SPONSORED RESEARCH OR DEVELOPMENT

Not applicable.

BACKGROUND OF THE INVENTION

1. Technical Field

The present invention relates to compositions of antimicrobial agents. More particularly the invention relates to formulations of an antimicrobial agent which render the drug potent against organisms normally considered to be resistant to the agent.

2. Background of the Invention

Based upon in vitro microbicidal sensitivity tests, the level of an antimicrobial drug considered effective against a particular organism may be determined. This is referred to as the MIC (minimum inhibitory concentration) of the drug. On the other hand, safety studies will determine the amount of drug that can be safely given to a patient or test animal. This maximal amount of drug that can be dosed will determine the maximal biological exposure to the host animal, normally measured by the area under the curve (AUC) of the plot of drug concentration vs. time, the peak height of the plot of drug concentration vs. time, tissue levels vs. time, etc. The instantaneous tissue or plasma level of the in vivo experiment can be compared with the MIC value to determine relative efficacy of the attainable drug levels in the biological fluids. The actual comparison must be corrected for plasma protein binding, inasmuch as only the free drug level is the important parameter because it is in this state that the drug is freely diffusible to cross biological membranes.

As a result of such analysis, clinical literature has been established specifying what drugs can be used generally for certain strains of organisms, or more precisely, for certain strains of organisms with MIC values below certain levels. As an example, the antifungal agent itraconazole is not considered effective for strains of *Candida albicans* with MIC>8 for this drug (e.g., for *C. albicans* strain c43 (ATCC number 201794), $MIC_{80}$=16 µg/ml for SPORANOX® itraconazole). These strains of *Candida albicans* are considered to be resistant to itraconazole. This presupposes the standard dosing level of this drug that can be administered.

However, if a method were available to substantially increase the amount of the antimicrobial drug (e.g., itraconazole) that could be administered, than it might be possible to treat infections hithertofore considered untreatable by this agent. Such a method is available through formulation of the drug as a nanosuspension. Submicron sized drug crystals stabilized by a surfactant coating have been found, in some cases, not to dissolve immediately upon injection into the blood stream. Instead, they are captured by fixed macrophages of the spleen and liver. From this sanctuary, the drug will be slowly released over a prolonged period of days. This is in contrast to conventionally solubilized drugs, which when injected, decrease in blood concentration at a much faster rate.

An example of an antimicrobial agent which is conventionally formulated to increase the solubility of the drug is the triazole antifungal agent itraconazole (FIG. 2). Itraconazole is effective against systemic mycoses, particularly aspergillosis and candidiasis. New oral and intravenous preparations of itraconazole have been prepared in order to overcome bioavailability problems associated with a lack of solubility. For example, the bioavailability of itraconazole is increased when it is formulated in hydroxypropyl-beta-cyclodextrin, a carrier oligosaccharide that forms an inclusion complex with the drug, thereby increasing its aqueous solubility. The commercial preparation is known by the tradename SPORANOX® Injection and was originated by JANSSEN PHARMACEUTICAL PRODUCTS, L.P. The drug is currently manufactured by Abbott Labs and distributed by Ortho Biotech, Inc.

Intravenous itraconazole may be useful in selected clinical situations. Examples are achlorhydria in AIDS patients, an inability to effectively absorb oral medications due to concurrent treatments with other drugs, or in critical-care patients who cannot take oral medications. The current commercial product, SPORANOX® Injection, is made available in 25 mL glass vials that contain 250 mg of itraconazole, with 10 g of hydroxypropyl-beta-cyclodextrin (referenced as "HPBCD"). These vials are diluted prior to use in 50 mL of 0.9% saline. The resulting cyclodextrin concentration exceeds 10% (w/v) in the reconstituted product. Although HPBCD has been traditionally regarded as safe for injection, high concentrations, such as 10%, have been reported in animal models to induce significant changes to endothelial tissues (Duncker G.; Reichelt J., Effects of the pharmaceutical cosolvent hydroxypropyl-beta-cyclodextrin on porcine corneal endothelium. (Graefe's Archive for Clinical and Experimental Opthalmology (Germany) 1998, 236/5, 380-389).

Other excipients are often used to formulate poorly water-soluble drugs for intravenous injection. For example, paclitaxel (Taxol®, produced by Bristol-Myers Squibb) contains 52.7% (w/v) of Cremophor® EL (polyoxyethylated castor oil) and 49.7% (v/v) dehydrated alcohol, USP. Administration of Cremophor® EL can lead to undesired hypersensitivity reactions (Volcheck, G. W., Van Dellen, R. G. Anaphylaxis to intravenous cyclosporine and tolerance to oral cyclosporine: case report and review. *Annals of Allergy, Asthma, and*

*Immunology,* 1998, 80, 159-163; Singla A. K.; Garg A.; Aggarwal D., Paclitaxel and its formulations. *International Journal of Pharmaceutics,* 2002, 235/1-2, 179-192).

The present invention discloses a composition which renders antimicrobial drugs more effective on the basis of their physical and biological properties than in their unformulated state or in their existing formulations. The approach used is to formulate the antimicrobial agents as nanosupensions. This permits using of the improved formulation to treat microbes conventionally thought to be resistant to the unformulated drug. Conventional formulation approaches attempt to enhance solubility or bioavailability only. Such methods include pH change, modification of the salt form, use of organic modifiers, or cyclodextrin. The approach disclosed in the present invention involves altering the pharmacokinetic characteristic of the drug, permitting far greater dosing, resulting in improved efficacy over and above what can be accomplished by improving solubility and bioavailability only. Acute toxicity tests have demonstrated that much more drug, when formulated as a nanosuspension, can be administered to animals. More of the drug is therefore available at the target organ to exert efficacy.

SUMMARY OF THE INVENTION

The present invention relates to a composition of an aqueous suspension of submicron- to micron-size particles of an antimicrobial agent that renders the agent potent against organisms normally considered to be resistant to the agent. The composition includes an aqueous suspension of submicron- to micron-size particles containing the agent coated with at least one surfactant selected from the group consisting of: ionic surfactants, non-ionic surfactants, biologically derived surfactants, and amino acids and their derivatives. The particles have a volume-weighted mean particle size of less than 5 µm as measured by light scattering (HORIBA) or by microscopic measurements. More preferably the particles should be less than about 1 micron and most preferably from about 150 nm to about 1 micron or any range or combination of ranges therein.

The present invention is suitable for pharmaceutical use.

In an embodiment of the invention, the antimicrobial agent is an antifungal agent. In a preferred embodiment, the antifungal agent is a triazole antifungal agent. In yet another embodiment of the invention, the triazole antifungal agent is selected from itraconazole, ketoconazole, miconazole, fluconazole, ravuconazole, voriconazole, saperconazole, eberconazole, genaconazole, clotrimazole, econazole, oxiconazole, sulconazole, terconazole, tioconazole, and posaconazole. In a preferred embodiment of the invention, the antifungal agent is itraconazole.

Suitable surfactants for coating the particles in the present invention can be selected from ionic surfactants, nonionic surfactants, biologically derived surfactants, or amino acids and their derivatives.

In a further preferred embodiment, the composition of the present invention is prepared by a microprecipitation method which includes the steps of: (i) dissolving in the antifungal agent in a first water-miscible first solvent to form a solution; (ii) mixing the solution with a second solvent which is aqueous to define a pre-suspension; and (iii) adding energy to the pre-suspension to form particles having an average effective particle size of less than 5 µm; more preferably less than about 1 micron, and most preferably from about 150 nm to about 1 micron or any range or combination of ranges therein, wherein the solubility of the antifungal agent is greater in the first solvent than in the second solvent, and the first solvent or the second solvent comprising one or more surfactants selected from the group consisting of: nonionic surfactants, ionic surfactants, biologically derived surfactants, and amino acids and their derivatives.

The present invention also relates to a method of rendering an antimicrobial agent potent against organisms normally considered to be resistant to the agent by formulating the agent as an aqueous suspension of submicron- to micron-size particles containing the agent coated with at least one surfactant selected from the group consisting of: ionic surfactants, non-ionic surfactants, biologically derived surfactants, and amino acids and their derivatives.

The present invention further relates to a method of treating infection of a subject by organisms normally considered to be resistant to an antimicrobial agent by administering the agent to the subject formulated as an aqueous suspension of submicron- to micron-size particles containing the agent coated with at least one surfactant selected from the group consisting of: ionic surfactants, non-ionic surfactants, biologically derived surfactants, and amino acids and their derivatives.

These and other aspects and attributes of the present invention will be discussed with reference to the following drawings and accompanying specification.

DETAILED DESCRIPTION OF THE PREFERRED EMBODIMENT

Figure 1:
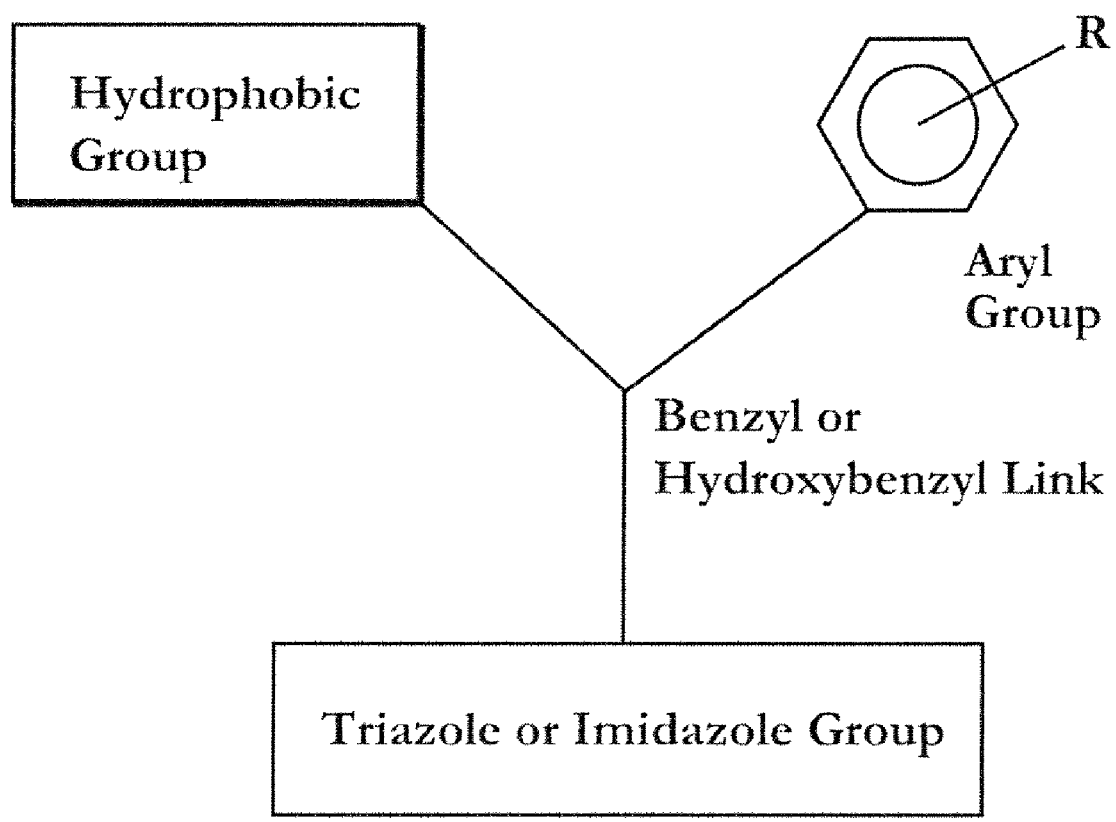
FIG. 1 is the general molecular structure of a triazole antifungal agent.

While this invention is susceptible of embodiment in many different forms, there are shown in the drawing, and will be described herein in detail, specific embodiments thereof with the understanding that the present disclosure is to be considered as an exemplification of the principles of the invention and is not intended to limit the invention to the specific embodiments illustrated.

The present invention relates to a composition of an antimicrobial agent that renders the agent potent against organisms normally considered to be resistant to the agent. The composition comprises an aqueous suspension of submicron-to micron-size particles containing the agent coated with at least one surfactant selected from the group consisting of: ionic surfactants, non-ionic surfactants, biologically derived surfactants, and amino acids and their derivatives. The composition disclosed in the present invention involves altering the pharmacokinetic characteristic of the drug, permitting far greater dosing, resulting in improved efficacy over and above what can be accomplished by improving solubility and bio-availability only. Submicron sized drug crystals stabilized by a surfactant coating have been found, in some cases, not to dissolve immediately upon injection into the blood stream. Instead, they are captured by fixed macrophages of the spleen and liver. From this sanctuary, the drug can be slowly released over a prolonged period of days. Acute toxicity tests have demonstrated that much more drug, when formulated as a nanosuspension, can be administered to animals or human beings. More of the drug is therefore available at the target organ to exert efficacy.

The particles in the present invention have a volume-weighted mean particle size of less than 5 μm as measured by light scattering (HORIBA) or by microscopic measurements. More preferably the particles should be less than about 1 micron and most preferably from about 150 nm to about 1 micron or any range or combination of ranges therein. The composition can be administered to a subject to treat infection by organisms normally considered to be resistant to the agent.

Figure 2:
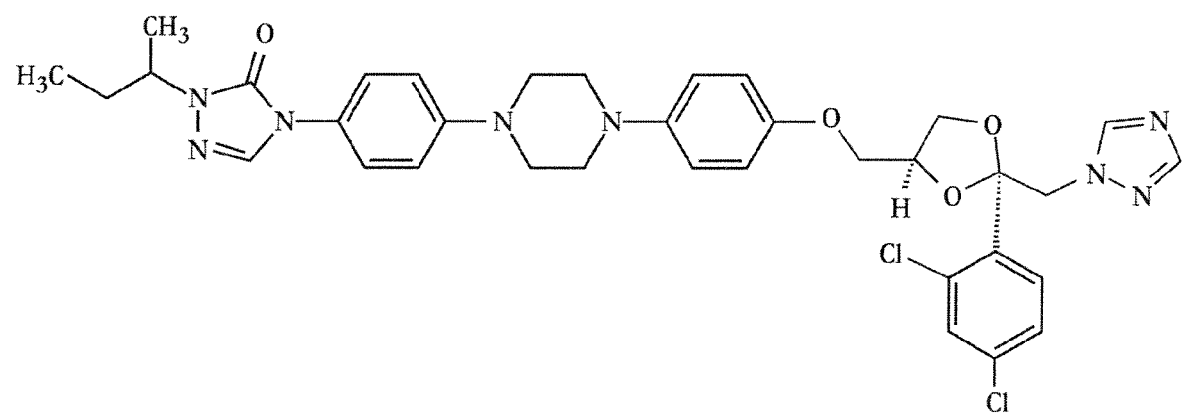
FIG. 2 is the molecular structure of itraconazole.

The antimicrobial agent is preferably a poorly water soluble organic compound. What is meant by "poorly water soluble" is that the water solubility of the compound is less than 10 mg/ml, and preferably, less than 1 mg/ml. A preferred class of antimicrobial agent is an antifungal agent. A preferred antifungal agent is the triazole antifungal agents having a general molecular structure as shown in FIG. 1. Examples of triazole antifungal agents include, but are not limited to: itraconazole, ketoconazole, miconazole, fluconazole, ravuconazole, voriconazole, saperconazole, eberconazole, genaconazole, clotrimazole, econazole, oxiconazole, sulconazole, terconazole, tioconazole, and posaconazole. A preferred antifungal agent for the present invention is itraconazole. The molecular structure of itraconazole is shown in FIG. 2.

The present invention is suitable for pharmaceutical use. The compositions can be administered by various routes, including but not limited to, intravenous, intracerebral, intrathecal, intralymphatic, pulmonary, intraarticular, and intraperitoneal. In an embodiment of the present invention, the aqueous medium of the composition is removed to form dry particles. The method to remove the aqueous medium can be any method known in the art. One example is evaporation. Another example is freeze drying or lyophilization. The dry particles may then be formulated into any acceptable physical form including, but is not limited to, solutions, tablets, capsules, suspensions, creams, lotions, emulsions, aerosols, powders, incorporation into reservoir or matrix devices for sustained release (such as implants or transdermal patches), and the like.

If the particles do not have to be taken up by the macrophages, the particles can be larger than 5 μm (e.g., less than 50 μm, or less than 7 μm) or less than 150 nm (e.g., less than 100 μm). These particles can be administered by various routes, including but not limited to parenteral, oral, buccal, periodontal, rectal, nasal, pulmonary, transdelinal, or topical. Modes of parenteral administration include intravenous, intra arterial, intrathecal, intraperitoneal, intraocular, intra articular, intrathecal, intracerebral, intramuscular, subcutaneous, and the like.

The aqueous suspension of the present invention may also be frozen to improve stability upon storage. Freezing of an aqueous suspension to improve stability is disclosed in the commonly assigned and co-pending U.S. Patent Application Ser. No. 60/347,548, which is incorporated herein by reference and made apart hereof.

In an embodiment of/be present invention, the antimicrobial agent is present in an amount preferably from about 0.01% to about 50% weight to volume (w/v), more preferably from about 0.05% to about 30% w/v, and most preferably from about 0.1% to about 20% w/v.

Suitable surfactants for coating the particles in the present invention can be selected from ionic surfactants, nonionic surfactants, biologically derived surfactants or amino acids and their derivatives. Ionic surfactants can be anionic, cationic, or zwitterionic.

Suitable anionic surfactants include but are not limited to: alkyl sulfonates, alkyl phosphates, alkyl phosphonates, potassium laurate, triethanolamine stearate, sodium lauryl sulfate, sodium dodecylsulfate, alkyl polyoxyethylene sulfates, sodium alginate, dioctyl sodium sulfosuccinate, phosphatidylglycerol, phosphatidylinosine, phosphatidylinositol, diphosphatidylglycerol, phosphatidylserine, phosphatidic acid and their salts, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.). As anionic surfactants, phospholipids may be used. Suitable phospholipids include, for example, phosphatidylserine, phosphatidylinositol, diphosphatidylglycerol, phosphatidylglycerol, or phosphatidic acid and its salts.

Zwitterionic surfactants are electrically neutral but posses local positive and negative charges within the same molecule. Suitable zwitterionic surfactants include but are not limited to zwitterionic phospholipids. Suitable phospholipids include phosphatidylcholine, phosphatidylethanolamine, diacyl-glycero-phosphoethanolamine (such as dimyristoyl-glycero-phosphoethanolamine (DMPE), dipalmitoyl-glycero-phosphoethanolamine (DPPE), distearoyl-glycero-phosphoethanolamine (DSPE), and dioleolyl-glycero-phosphoethanolamine (DOPE)). Mixtures of phospholipids that include anionic and zwitterionic phospholipids may be employed in this invention. Such mixtures include but are not limited to lysophospholipids, egg or soybean phospholipid or any combination thereof. The phospholipid, whether anionic, zwitterionic or a mixture of phospholipids, may be salted or desalted, hydrogenated or partially hydrogenated or natural semisynthetic or synthetic. The phospholipid may also be conjugated with a water-soluble or hydrophilic polymer to specifically target the delivery to macrophages in the present invention. However, conjugated phospholipids may be used to target other cells or tissue in other applications. A preferred polymer is polyethylene glycol (PEG), which is also known as the monomethoxy polyethyleneglycol (mPEG). The molecule weights of the PEG can vary, for example, from 200 to 50,000. Some commonly used PEG's that are commercially available include PEG 350, PEG 550, PEG 750, PEG 1000, PEG 2000, PEG 3000, and PEG 5000. The phospholipid or the PEG-phospholipid conjugate may also incorporate a functional group which can covalently attach to a ligand including but not limited to proteins, peptides, carbohydrates, glycoproteins, antibodies, or pharmaceutically active agents. These functional groups may conjugate with the ligands through, for example, amide bond formation, disulfide or thioether formation, or biotin/streptavidin binding. Examples of the ligand-binding functional groups include but are not limited to hexanoylamine, dodecanylamine, 1,12-dodecanedicarboxylate, thioethanol, 4-(p-maleimidophenyl)butyramide (MPB), 4-(p-maleimidomethyl)cyclohexane-carboxamide (MCC), 3-(2-pyridyldithio)propionate (PDP), succinate, glutarate, dodecanoate, and biotin.

Suitable cationic surfactants include but are not limited to quaternary ammonium compounds, such as benzalkonium chloride, cetyltrimethylammonium bromide, lauryldimethylbenzylammonium chloride, acyl carnitine hydrochlorides, or alkyl pyridinium halides, or long-chain alkyl amines such as, for example, n-octylamine and oleylamine.

Suitable nonionic surfactants include: glyceryl esters, polyoxyethylene fatty alcohol ethers (Macrogol and Brij), polyoxyethylene sorbitan fatty acid esters (Polysorbates), polyoxyethylene fatty acid esters (Myrj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), poloxamines, methylcellulose, hydroxymethylcellulose, hydroxypropylcellulose, hydroxypropylmethylcellulose, noncrystalline cellulose, polysaccharides including starch and starch derivatives such as hydroxyethylstarch (HES), polyvinyl alcohol, and polyvinylpyrrolidone. In a preferred form of the invention, the nonionic surfactant is a polyoxyethylene and polyoxypropylene copolymer and preferably a block copolymer of propylene glycol and ethylene glycol. Such polymers are sold under the tradename POLOXAMER also sometimes referred to as PLURONIC®, and sold by several suppliers including Spectrum Chemical and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft.

Surface-active biological molecules include such molecules as albumin, casein, hirudin or other appropriate proteins. Polysaccharide biologics are also included, and consist of but are not limited to, starches, heparin and chitosans. Other suitable surfactants include any amino acids such as leucine, alanine, valine, isoleucine, lysine, aspartic acid, glutamic acid, methionine, phenylalanine, or any derivatives of these amino acids such as, for example, amide or ester derivatives and polypeptides formed from these amino acids.

A preferred ionic surfactant is a bile salt, and a preferred bile salt is deoxycholate. A preferred nonionic surfactant is a polyalkoxyether, and a preferred polyalkoxyether is Poloxamer 188. Another preferred nonionic surfactant is Solutol HS 15 (polyethylene-660-hydroxystearate). Still yet another preferred nonionic surfactant is hydroxyethylstarch. A preferred biologically derived surfactant is albumin.

In another embodiment of the present invention, the surfactants are present in an amount of preferably from about 0.001% to 5% w/v, more preferably from about 0.005% to about 5% w/v, and most preferably from about 0.01% to 5% w/v.

In a preferred embodiment of the present invention, the particles are suspended in an aqueous medium further including a pH adjusting agent. Suitable pH adjusting agents include, but are not limited to, hydrochloric acid, sulfuric acid, phosphoric acid, monocarboxylic acids (such as, for example, acetic acid and lactic acid), dicarboxylic acids (such as, for example, succinic acid), tricarboxylic acids (such as, for example, citric acid), THAM (tris(hydroxymethyl)aminomethane), meglumine (N-methylglucosamine), sodium hydroxide, and amino acids such as glycine, arginine, lysine, alanine, histidine and leucine. The aqueous medium may additionally include an osmotic pressure adjusting agent, such as but not limited to glycerin, a monosaccharide such as dextrose, a disaccharide such as sucrose, a trisaccharide such as raffinose, and sugar alcohols such as mannitol, xylitol and sorbitol.

In a preferred embodiment of the present invention, the composition comprises an aqueous suspension of particles of itraconazole present at 0.01 to 50% w/v, the particles are coated with 0.001 to 5% w/v of a bile salt (e.g., deoxycholate) and 0.001 to 5% w/v polyalkoxyether (for example, Poloxamer 188), and glycerin added to adjust osmotic pressure of the formulation.

In another preferred embodiment of the present invention, the composition comprises an aqueous suspension of particles of itraconazole present at about 0.01 to 50% w/v, the particles coated with about 0.001 to 5% w/v of a bile salt (for example, deoxycholate) and 0.001 to 5% polyethylene-660-hydroxystearate w/v, and glycerin added to adjust osmotic pressure of the formulation.

In another preferred embodiment of the present invention, the composition comprises an aqueous suspension of itraconazole present at about 0:01 to 50% w/v, the particles are coated with about 0.001 to 5% of polyethylene-660-hydroxystearate w/v, and glycerin added to adjust osmotic pressure of the formulation.

In still yet another preferred embodiment of the present invention, the composition comprises an aqueous suspension of itraconazole present at 0.01 to 50% w/v, the particles are coated with about 0.001 to 5% albumin w/v.

The method for preparing the suspension in the present invention is disclosed in commonly assigned and co-pending U.S. Patent Application Ser. Nos. 60/258,160; 09/874,799; 09/874,637; 09/874,499; 09/964,273; 10/035,821; 60/347,548; 10/021,692; 10/183,035; 10/213,352; 10/246,802; 10/270,268; 10/270,267, and 10/390,333; which are incorporated herein by reference and made a part hereof. A general procedure for preparing the suspension useful in the practice of this invention follows.

The processes can be separated into three general categories. Each of the categories of processes share the steps of: (1) dissolving an antifungal agent in a water miscible first organic solvent to create a first solution; (2) mixing the first solution with a second solvent of water to precipitate the antifungal agent to create a pre-suspension; and (3) adding energy to the presuspension in the form of high-shear mixing or heat to provide a stable form of the antifungal agent having the desired size ranges defined above.

The three categories of processes are distinguished based upon the physical properties of the antifungal agent as determined through x-ray diffraction studies, differential scanning calorimetry (DSC) studies or other suitable study conducted prior to the energy-addition step and after the energy-addition step. In the first process category, prior to the energy-addition step the antifungal agent in the presuspension takes an amorphous form, a semi-crystalline form or a supercooled liquid form and has an average effective particle size. After the energy-addition step, the antifungal agent is in a crystalline form having an average effective particle size essentially the same as that of the presuspension (i.e., from less than about 50 µm).

In the second process category, prior to the energy-addition step the antifungal agent is in a crystalline form and has an average effective particle size. After the energy-addition step, the antifungal agent is in a crystalline form having essentially the same average effective particle size as prior to the energy-addition step but the crystals after the energy-addition step are less likely to aggregate.

The lower tendency of the organic compound to aggregate is observed by laser dynamic light scattering and light microscopy.

In the third process category, prior to the energy-addition step the antifungal agent is in a crystalline form that is friable and has an average effective particle size. What is meant by the term "friable" is that the particles are fragile and are more easily broken down into smaller particles. After the energy-addition step the organic compound is in a crystalline form having an average effective particle size smaller than the crystals of the pre-suspension. By taking the steps necessary to place the organic compound in a crystalline form that is friable, the subsequent energy-addition step can be carried out more quickly and efficiently when compared to an organic compound in a less friable crystalline morphology.

The energy-addition step can be carried out in any fashion wherein the pre-suspension is exposed to cavitation, shearing or impact forces. In one preferred form of the invention, the energy-addition step is an annealing step. Annealing is defined in this invention as the process of converting matter that is thermodynamically unstable into a more stable form by single or repeated application of energy (direct heat or mechanical stress), followed by thermal relaxation. This lowering of energy may be achieved by conversion of the solid form from a less ordered to a more ordered lattice structure. Alternatively, this stabilization may occur by a reordering of the surfactant molecules at the solid-liquid interface.

These three process categories will be discussed separately below. It should be understood, however, that the process conditions such as choice of surfactants or combination of surfactants, amount of surfactant used, temperature of reaction, rate of mixing of solutions, rate of precipitation and the like can be selected to allow for any drug to be processed under any one of the categories discussed next.

Figure 3:
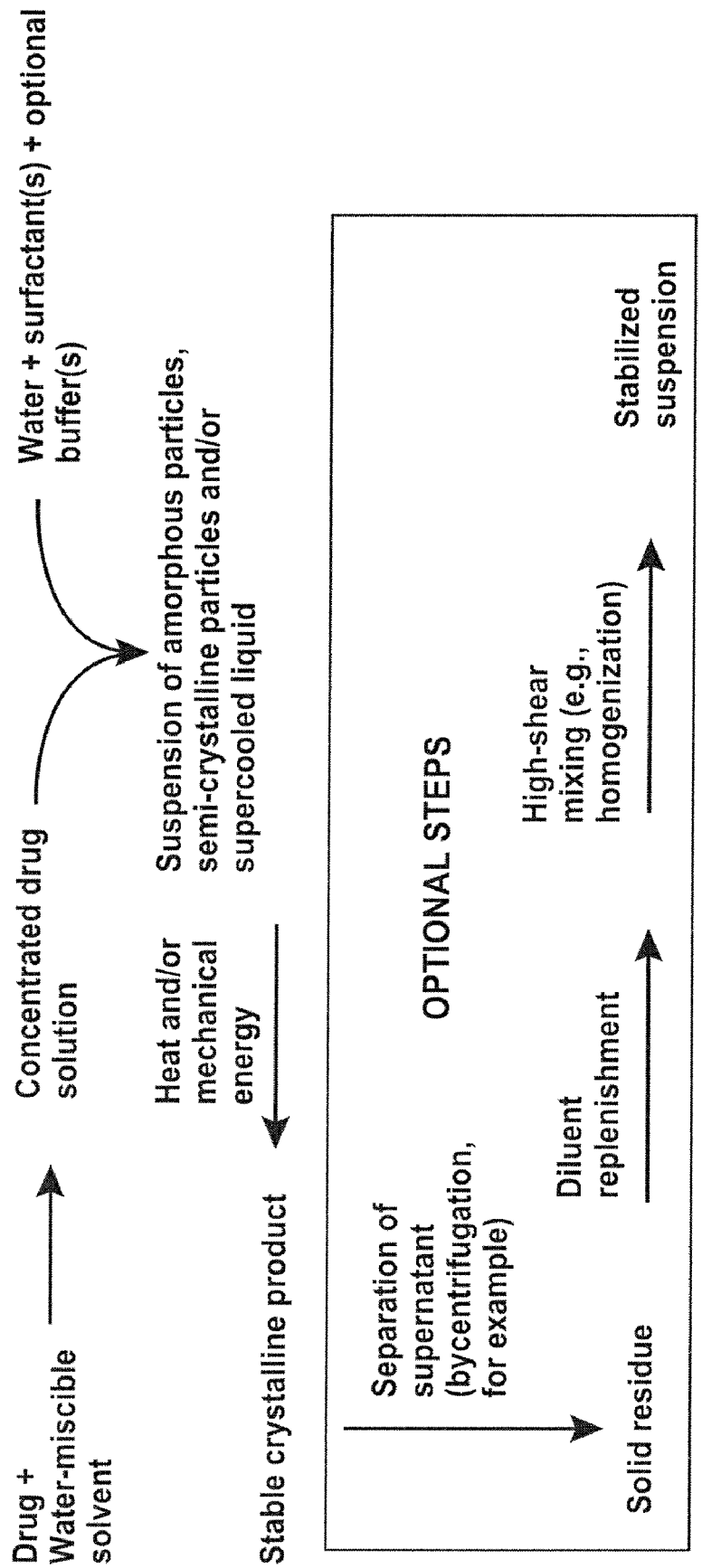
FIG. 3 is a schematic diagram of Method A of the microprecipitation process used in the present invention to prepare the suspension.
Figure 4:
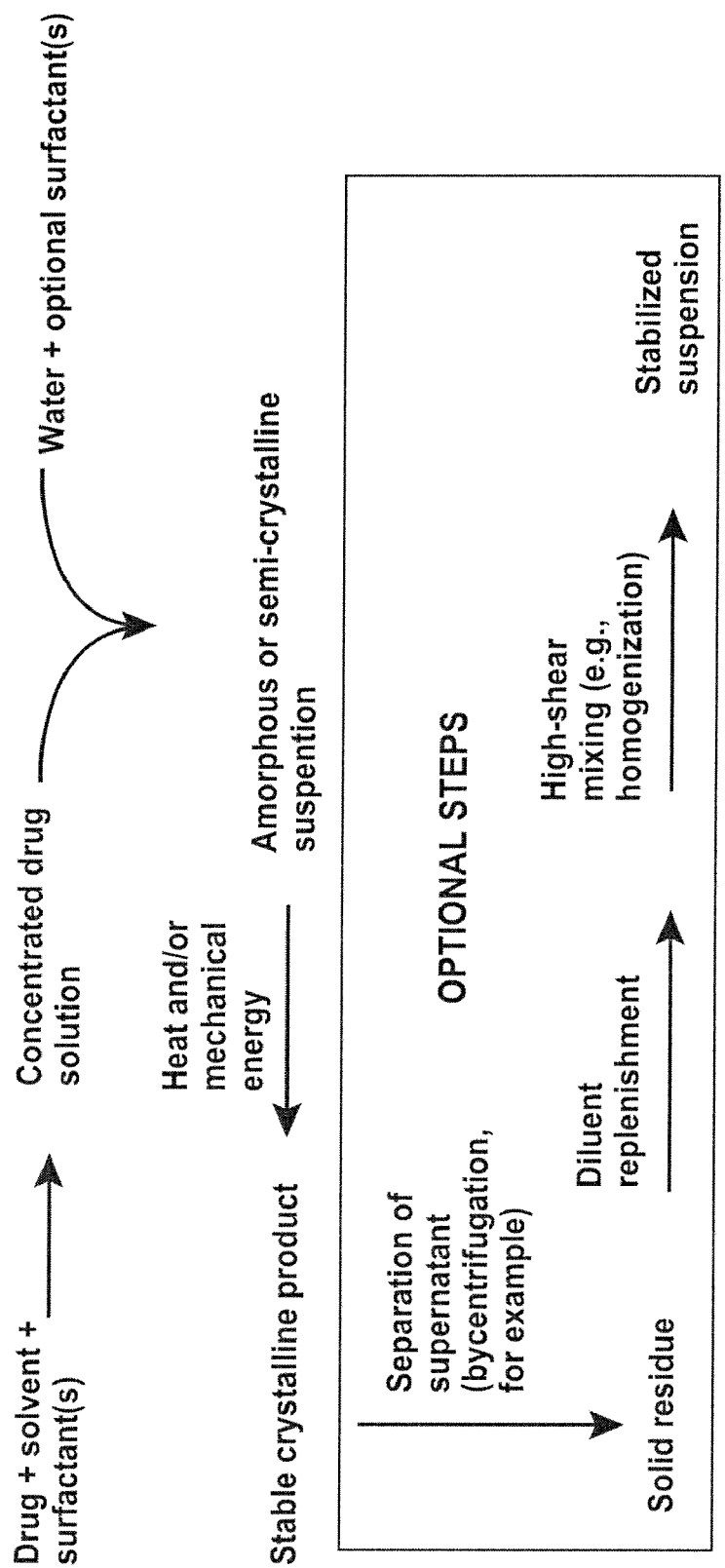
FIG. 4 is a schematic diagram of Method B of the microprecipitation process used in the present invention to prepare the suspension.

The first process category, as well as the second and third process categories, can be further divided into two subcategories, Method A, and B shown diagrammatically in FIG. 3 and FIG. 4, respectively.

The first solvent according to the present invention is a solvent or mixture of solvents in which the organic compound of interest is relatively soluble and which is miscible with the second solvent. Such solvents include, but are not limited to water-miscible protic compounds, in which a hydrogen atom in the molecule is bound to an electronegative atom such as oxygen, nitrogen, or other Group VA, VIA and VII A in the Periodic Table of elements. Examples of such solvents include, but are not limited to, alcohols, amines (primary or secondary), oximes, hydroxamic acids, carboxylic acids, sulfonic acids, phosphonic acids, phosphoric acids, amides and ureas.

Other examples of the first solvent also include aprotic organic solvents. Some of these aprotic solvents can form hydrogen bonds with water, but can only act as proton acceptors because they lack effective proton donating groups. One class of aprotic solvents is a dipolar aprotic solvent, as defined by the International Union of Pure and Applied Chemistry (IUPAC Compendium of Chemical Terminology, 2nd Ed., 1997):

A solvent with a comparatively high relative permittivity (or dielectric constant), greater than ca. 15, and a sizable permanent dipole moment, that cannot donate suitably labile hydrogen atoms to form strong hydrogen bonds, e.g. dimethyl sulfoxide.

Dipolar aprotic solvents can be selected from the group consisting of: amides (fully substituted, with nitrogen lacking attached hydrogen atoms), ureas (fully substituted, with no hydrogen atoms attached to nitrogen), ethers, cyclic ethers, nitriles, ketones, sulfones, sulfoxides, fully substituted phosphates, phosphonate esters, phosphoramides, nitro compounds, and the like. Dimethylsulfoxide (DMSO), N-methyl-2-pyrrolidinone (NMP), 2-pyrrolidinone, 1,3-dimethylimidazolidinone (DMI), dimethylacetamide (DMA), dimethylformamide (DMF), dioxane, acetone, tetrahydrofuran (THF), tetramethylenesulfone (sulfolane), acetonitrile, and hexamethylphosphoramide (HMPA), nitromethane, among others, are members of this class.

Solvents may also be chosen that are generally water-immiscible, but have sufficient water solubility at low volumes (less than 10%) to act as a water-miscible first solvent at these reduced volumes. Examples include aromatic hydrocarbons, alkenes, alkanes, and halogenated aromatics, halogenated alkenes and halogenated alkanes. Aromatics include, but are not limited to, benzene (substituted or unsubstituted), and monocyclic or polycyclic arenes. Examples of substituted benzenes include, but are not limited to, xylenes (ortho, meta, or para), and toluene. Examples of alkanes include but are not limited to hexane, neopentane, heptane, isooctane, and cyclohexane. Examples of halogenated aromatics include, but are not restricted to, chlorobenzene, bromobenzene, and chlorotoluene. Examples of halogenated alkanes and alkenes include, but are not restricted to, trichloroethane, methylene chloride, ethylenedichloride (EDC), and the like.

Examples of the all of the above solvent classes include but are not limited to: N-methyl-2-pyrrolidinone (also called N-methyl-2-pyrrolidone), 2-pyrrolidinone (also called 2-pyrrolidone), 1,3-dimethyl-2-imidazolidinone (DMI), dimethylsulfoxide, dimethylacetamide, carboxylic acids (such as acetic acid and lactic acid), aliphatic alcohols (such as methanol, ethanol, isopropanol, 3-pentanol, and n-propanol), benzyl alcohol, glycerol, butylene glycol (butanediol), ethylene glycol, propylene glycol, mono- and diacylated monoglycerides (such as glyceryl caprylate), dimethyl isosorbide, acetone, dimethylsulfone, dimethylformamide, 1,4-dioxane, tetramethylenesulfone (sulfolane), acetonitrile, nitromethane, tetramethylurea, hexamethylphosphoramide (HMPA), tetrahydrofuran (THF), dioxane, diethylether, tert-butylmethyl ether (TBME), aromatic hydrocarbons, alkenes, alkanes, halogenated aromatics, halogenated alkenes, halogenated alkanes, xylene, toluene, benzene, substituted benzene, ethyl acetate, methyl acetate, butyl acetate, chlorobenzene, bromobenzene, chlorotoluene, trichloroethane, methylene chloride, ethylenedichloride (EDC), hexane, neopentane, heptane, isooctane, cyclohexane, polyethylene glycol (PEG, for example, PEG-4, PEG-8, PEG-9, PEG-12, PEG-14, PEG-16, PEG- 120, PEG-75, PEG-150), polyethylene glycol esters (examples such as PEG-4 dilaurate, PEG-20 dilaurate, PEG-6 isostearate, PEG-8 palmitostearate, PEG-150 palmitostearate), polyethylene glycol sorbitans (such as PEG-20 sorbitan isostearate), polyethylene glycol monoalkyl ethers (examples such as PEG-3 dimethyl ether, PEG-4 dimethyl ether), polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether). A preferred first solvent is N-methyl-2-pyrrolidinone. Another preferred first solvent is lactic acid.

The second solvent is an aqueous solvent. This aqueous solvent may be water by itself. This solvent may also contain buffers, salts, surfactant(s), water-soluble polymers, and combinations of these excipients.

Method A

In Method A (see FIG. 3), the antimicrobial agent is first dissolved in the first solvent to create a first solution. The antimicrobial agent can be added from about 0.01% (w/v) to about 50% (w/v) depending on the solubility of the antimicrobial agent in the first solvent. Heating of the concentrate from about 30° C. to about 100° C. may be necessary to ensure total dissolution of the antimicrobial agent in the first solvent.

A second aqueous solution is provided with one or more surfactants added thereto. The surfactants can be selected from an ionic surfactant, a nonionic surfactant or a biologically derived surfactant set forth above.

It may also be desirable to add a pH adjusting agent to the second solution such as sodium hydroxide, hydrochloric acid, tris buffer or citrate, acetate, lactate, meglumine, or the like. The second solution should have a pH within the range of from about 3 to about 11.

In a preferred form of the invention, the method for preparing submicron sized particles of an antimicrobial agent includes the steps of adding the first solution to the second solution. The addition rate is dependent on the batch size, and precipitation kinetics for the antimicrobial agent. Typically, for a small-scale laboratory process (preparation of 1 liter), the addition rate is from about 0.05 cc per minute to about 10 cc per minute. During the addition, the solutions should be under constant agitation. It has been observed using light microscopy that amorphous particles, semi-crystalline solids, or a supercooled liquid are formed to create a pre-suspension. The method further includes the step of subjecting the pre-suspension to an annealing step to convert the amorphous particles, supercooled liquid or semicrystalline solid to a crystalline more stable solid state. The resulting particles will have an average effective particles size as measured by dynamic light scattering methods (e.g., photocorrelation spectroscopy, laser diffraction, low-angle laser light scattering (LALLS), medium-angle laser light scattering (MALLS), light obscuration methods (Coulter method, for example), theology, or microscopy (light or electron) within the ranges set forth above).

The energy-addition step involves adding energy through sonication, homogenization, counter current flow homogenization (e.g., the Mini DeBEE 2000 homogenizer, available from BEE Incorporated, NC, in which a jet of fluid is directed along a first path, and a structure is interposed in the first path to cause the fluid to be redirected in a controlled flow path along a new path to cause emulsification or mixing of the fluid), microfluidization, or other methods of providing impact, shear or cavitation forces. The sample may be cooled or heated during this stage. In one preferred form of the invention the annealing step is effected by homogenization. In another preferred form of the invention the annealing may be accomplished by ultrasonication. In yet another preferred form of the invention the annealing may be accomplished by use of an emulsification apparatus as described in U.S. Pat. No. 5,720,551 which is incorporated herein by reference and made a part hereof.

Depending upon the rate of annealing, it may be desirable to adjust the temperature of the processed sample to within the range of from approximately −30° C. to 100° C. Alternatively, in order to effect a desired phase change in the processed solid, it may also be necessary to adjust the temperature of the pre-suspension to a temperature within the range of from about −30° C. to about 100° C. during the annealing step.

Method B

Method B differs from Method A in the following respects. The first difference is a surfactant or combination of surfactants are added to the first solution. The surfactants may be selected from ionic surfactants, nonionic surfactants, or biologically derived as set forth above.

A drug suspension resulting from application of the processes described in this invention may be administered directly as an injectable solution, provided Water for Injection is used in formulation and an appropriate means for solution sterilization is applied. Sterilization may be accomplished by separate sterilization of the drug concentrate (drug, solvent, and optional surfactant) and the diluent medium (water, and optional buffers and surfactants) prior to mixing to form the pre-suspension. Sterilization methods include pre-filtration first through a 3.0 micron filter followed by filtration through a 0.45-micron particle filter, followed by steam or heat sterilization or sterile filtration through two redundant 0.2-micron membrane filters.

Optionally, a solvent-free suspension may be produced by solvent removal after precipitation. This can be accomplished by centrifugation, dialysis, diafiltration, force-field fractionation, high-pressure filtration or other separation techniques well known in the art. Complete removal of N-methyl-2-pyrrolidinone was typically carried out by one to three successive centrifugation runs; after each centrifugation the supernatant was decanted and discarded. A fresh volume of the suspension vehicle without the organic solvent was added to the remaining solids and the mixture was dispersed by homogenization. It will be recognized by others skilled in the art that other high-shear mixing techniques could be applied in this reconstitution step.

Furthermore, any undesired excipients such as surfactants may be replaced by a more desirable excipient by use of the separation methods described in the above paragraph. The solvent and first excipient may be discarded with the supernatant after centrifugation or filtration. A fresh volume of the suspension vehicle without the solvent and without the first excipient may then be added. Alternatively, a new surfactant may be added. For example, a suspension consisting of drug, N-methyl-2-pyrrolidinone (solvent), Poloxamer 188 (first excipient), sodium deoxycholate, glycerol and water may be replaced with phospholipids (new surfactant), glycerol and water after centrifugation and removal of the supernatant.

I. First Process Category

The methods of the first process category generally include the step of dissolving the antimicrobial agent in a water miscible first solvent followed by the step of mixing this solution with an aqueous solution to a presuspension wherein the antimicrobial agent is in an amorphous form, a semicrystalline form or in a supercooled liquid form as determined by x-ray diffraction studies, DSC, light microscopy or other analytical techniques and has an average effective particle size within one of the effective particle size ranges set forth above. The mixing step is followed by an energy-addition step and, in a preferred form of the invention is an annealing step.

II. Second Process Category

The methods of the second processes category include essentially the same steps as in the steps of the first processes category but differ in the following respect. An x-ray diffraction, DSC or other suitable analytical techniques of the presuspension shows the antimicrobial agent in a crystalline form and having an average effective particle size. The antimicrobial agent after the energy-addition step has essentially the same average effective particle size as prior to the energy-addition step but has less of a tendency to aggregate into larger particles when compared to that of the particles of the presuspension. Without being bound to a theory, it is believed the differences in the particle stability may be due to a reordering of the surfactant molecules at the solid-liquid interface.

III. Third Process Category

The methods of the third category modify the first two steps of those of the first and second processes categories to ensure the antimicrobial agent in the presuspension is in a friable form having an average effective particle size (e.g., such as slender needles and thin plates). Friable particles can be formed by selecting suitable solvents, surfactants or combination of surfactants, the temperature of the individual solutions, the rate of mixing and rate of precipitation and the like. Friability may also be enhanced by the introduction of lattice defects (e.g., cleavage planes) during the steps of mixing the first solution with the aqueous solution. This would arise by rapid crystallization such as that afforded in the precipitation step. In the energy-addition step these friable crystals are converted to crystals that are kinetically stabilized and having an average effective particle size smaller than those of the presuspension. Kinetically stabilized means particles have a reduced tendency to aggregate when compared to particles that are not kinetically stabilized. In such instance the energy-addition step results in a breaking up of the friable particles. By ensuring the particles of the presuspension are in a friable state, the organic compound can more easily and more quickly be prepared into a particle within the desired size ranges when compared to processing an organic compound where the steps have not been taken to render it in a friable form.

In addition to the microprecipitation methods described above, any other known precipitation methods for preparing submicron sized particles or nanoparticles in the art can be used in conjunction with the present invention. The following is a description of examples of other precipitation methods. The examples are for illustration purposes, and are not intended to limit the scope of the present invention.

Emulsion Precipitation Methods

One suitable emulsion precipitation technique is disclosed in the co-pending and commonly assigned U.S. Ser. No. 09/964,273, which is incorporated herein by reference and is made a part hereof. In this approach, the process includes the steps of: (1) providing a multiphase system having an organic phase and an aqueous phase, the organic phase having a pharmaceutically effective compound therein; and (2) sonicating the system to evaporate a portion of the organic phase to cause precipitation of the compound in the aqueous phase and having an average effective particle size of less than about 2 µm. The step of providing a multiphase system includes the steps of: (1) mixing a water immiscible solvent with the pharmaceutically effective compound to define an organic solution, (2) preparing an aqueous based solution with one or more surface active compounds, and (3) mixing the organic solution with the aqueous solution to form the multiphase system. The step of mixing the organic phase and the aqueous phase can include the use of piston gap homogenizers, colloidal mills, high speed stirring equipment, extrusion equipment, manual agitation or shaking equipment, microfluidizer, or other equipment or techniques for providing high shear conditions. The crude emulsion will have oil droplets in the water of a size of approximately less than 1 µM in diameter. The crude emulsion is sonicated to define a microemulsion and eventually to define a submicron sized particle suspension.

Another approach to preparing submicron sized particles is disclosed in co-pending and commonly assigned U.S. Ser. No. 10/183,035, which is incorporated herein by reference and made a part hereof. The process includes the steps of: (1) providing a crude dispersion of a multiphase system having an organic phase and an aqueous phase, the organic phase having a pharmaceutical compound therein; (2) providing energy to the crude dispersion to form a fine dispersion; (3) freezing the fine dispersion; and (4) lyophilizing the fine dispersion to obtain submicron sized particles of the pharmaceutical compound. The step of providing a multiphase system includes the steps of: (1) mixing a water immiscible solvent with the pharmaceutically effective compound to define an organic solution; (2) preparing an aqueous based solution with one or more surface active compounds; and (3) mixing the organic solution with the aqueous solution to form the multiphase system. The step of mixing the organic phase and the aqueous phase includes the use of piston gap homogenizers, colloidal mills, high speed stirring equipment, extrusion equipment, manual agitation or shaking equipment, microfluidizer, or other equipment or techniques for providing high shear conditions.

Solvent Anti-Solvent Precipitation

Suitable solvent anti-solvent precipitation technique is disclosed in U.S. Pat. Nos. 5,118,528 and 5,100,591 which are incorporated herein by reference and made a part hereof. The process includes the steps of: (1) preparing a liquid phase of a biologically active substance in a solvent or a mixture of solvents to which may be added one or more surfactants; (2) preparing a second liquid phase of a non-solvent or a mixture of non-solvents, the non-solvent is miscible with the solvent or mixture of solvents for the substance; (3) adding together the solutions of (1) and (2) with stirring; and (4) removing of unwanted solvents to produce a colloidal suspension of nanoparticles. The '528 patent discloses that it produces particles of the substance smaller than 500 nm without the supply of energy.

Phase Inversion Precipitation

One suitable phase inversion precipitation is disclosed in U.S. Pat. Nos. 6,235,224, 6,143,211 and U.S. patent application No. 2001/0042932 which are incorporated herein by reference and made apart hereof. Phase inversion is a term used to describe the physical phenomena by which a polymer dissolved in a continuous phase solvent system inverts into a solid macromolecular network in which the polymer is the continuous phase. One method to induce phase inversion is by the addition of a nonsolvent to the continuous phase. The polymer undergoes a transition from a single phase to an unstable two phase mixture: polymer rich and polymer poor fractions. Micellar droplets of nonsolvent in the polymer rich phase serve as nucleation sites and become coated with polymer. The '224 patent discloses that phase inversion of polymer solutions under certain conditions can bring about spontaneous formation of discrete microparticles, including nanoparticles. The '224 patent discloses dissolving or dispersing a polymer in a solvent. A pharmaceutical agent is also dissolved or dispersed in the solvent. For the crystal seeding step to be effective in this process it is desirable the agent is dissolved in the solvent. The polymer, the agent and the solvent together form a mixture having a continuous phase, wherein the solvent is the continuous phase. The mixture is then introduced into at least tenfold excess of a miscible nonsolvent to cause the spontaneous formation of the microencapsulated microparticles of the agent having an average particle size of between 10 nm and 10 µm. The particle size is influenced by the solvent:nonsolvent volume ratio, polymer concentration, the viscosity of the polymer-solvent solution, the molecular weight of the polymer, and the characteristics of the solvent-nonsolvent pair. The process eliminates the step of creating microdroplets, such as by forming an emulsion, of the solvent. The process also avoids the agitation and/or shear forces.

pH Shift Precipitation pH shift precipitation techniques typically include a step of dissolving a drug in a solution having a pH where the drug is soluble, followed by the step of changing the pH to a point where the drug is no longer soluble. The pH can be acidic or basic, depending on the particular pharmaceutical compound. The solution is then neutralized to form a presuspension of submicron sized particles of the pharmaceutically active compound. One suitable pH shifting precipitation process is disclosed in U.S. Pat. No. 5,665,331, which is incorporated herein by reference and made a part hereof. The process includes the step of dissolving of the pharmaceutical agent together with a crystal growth modifier (CGM) in an alkaline solution and then neutralizing the solution with an acid in the presence of suitable surface-modifying surface-active agent or agents to form a fine particle dispersion of the pharmaceutical agent. The precipitation step can be followed by steps of diafiltration clean-up of the dispersion and then adjusting the concentration of the dispersion to a desired level. This process of reportedly leads to microcrystalline particles of Z-average diameters smaller than 400 nm as measured by photon correlation spectroscopy.

Other examples of pH shifting precipitation methods are disclosed in U.S. Pat. Nos. 5,716,642; 5,662,883; 5,560,932; and 4,608,278, which are incorporated herein by reference and are made a part hereof.

Infusion Precipitation Method

Suitable infusion precipitation techniques are disclosed in the U.S. Pat. Nos. 4,997,454 and 4,826,689, which are incorporated herein by reference and made a part hereof. First, a suitable solid compound is dissolved in a suitable organic solvent to form a solvent mixture. Then, a precipitating nonsolvent miscible with the organic solvent is infused into the solvent mixture at a temperature between about −10° C. and about 100° C. and at an infusion rate of from about 0.01 ml per minute to about 1000 ml per minute per volume of 50 ml to produce a suspension of precipitated non-aggregated solid particles of the compound with a substantially uniform mean diameter of less than 10 µm. Agitation (e.g., by stirring) of the solution being infused with the precipitating nonsolvent is preferred. The nonsolvent may contain a surfactant to stabilize the particles against aggregation. The particles are then separated from the solvent. Depending on the solid compound and the desired particle size, the parameters of temperature, ratio of nonsolvent to solvent, infusion rate, stir rate, and volume can be varied according to the invention. The particle size is proportional to the ratio of nonsolvent:solvent volumes and the temperature of infusion and is inversely proportional to the infusion rate and the stirring rate. The precipitating nonsolvent may be aqueous or non-aqueous, depending upon the relative solubility of the compound and the desired suspending vehicle.

Temperature Shift Precipitation

Temperature shift precipitation technique, also known as the hot-melt technique, is disclosed in U.S. Pat. No. 5,188,837 to Domb, which is incorporated herein by reference and made a part hereof. In an embodiment of the invention, lipospheres are prepared by the steps of: (1) melting or dissolving a substance such as a drug to be delivered in a molten vehicle to form a liquid of the substance to be delivered; (2) adding a phospholipid along with an aqueous medium to the melted substance or vehicle at a temperature higher than the melting temperature of the substance or vehicle; (3) mixing the suspension at a temperature above the melting temperature of the vehicle until a homogenous fine preparation is obtained; and then (4) rapidly cooling the preparation to room temperature or below.

Solvent Evaporation Precipitation

Solvent evaporation precipitation techniques are disclosed in U.S. Pat. No. 4,973,465 which is incorporated herein by reference and made apart hereof. The '465 patent discloses methods for preparing microcrystals including the steps of: (1) providing a solution of a pharmaceutical composition and a phospholipid dissolved in a common organic solvent or combination of solvents, (2) evaporating the solvent or solvents and (3) suspending the film obtained by evaporation of the solvent or solvents in an aqueous solution by vigorous stirring. The solvent can be removed by adding energy to the solution to evaporate a sufficient quantity of the solvent to cause precipitation of the compound. The solvent can also be removed by other well known techniques such as applying a vacuum to the solution or blowing nitrogen over the solution.

Reaction Precipitation

Reaction precipitation includes the steps of dissolving the pharmaceutical compound into a suitable solvent to form a solution. The compound should be added in an amount at or below the saturation point of the compound in the solvent. The compound is modified by reacting with a chemical agent or by modification in response to adding energy such as heat or UV light or the like to such that the modified compound has a lower solubility in the solvent and precipitates from the solution.

Compressed Fluid Precipitation

A suitable technique for precipitating by compressed fluid is disclosed in WO 97/14407 to Johnston, which is incorporated herein by reference and made a part hereof. The method includes the steps of dissolving a water-insoluble drug in a solvent to form a solution. The solution is then sprayed into a compressed fluid, which can be a gas, liquid or supercritical fluid. The addition of the compressed fluid to a solution of a solute in a solvent causes the solute to attain or approach supersaturated state and to precipitate out as fine particles. In this case, the compressed fluid acts as an anti-solvent which lowers the cohesive energy density of the solvent in which the drug is dissolved.

Alternatively, the drug can be dissolved in the compressed fluid which is then sprayed into an aqueous phase. The rapid expansion of the compressed fluid reduces the solvent power of the fluid, which in turn causes the solute to precipitate out as fine particles in the aqueous phase. In this case, the compressed fluid acts as a solvent.

Other Methods for Preparing Particles

The particles of the present invention can also be prepared by mechanical grinding of the active agent. Mechanical grinding include such techniques as jet milling, pearl milling, ball milling, hammer milling, fluid energy milling or wet grinding techniques such as those disclosed in U.S. Pat. No. 5,145,684, which is incorporated herein by reference and made a part hereof.

Another method to prepare the particles of the present invention is by suspending an active agent. In this method, particles of the active agent are dispersed in an aqueous medium by adding the particles directly into the aqueous medium to derive a pre-suspension. The particles are normally coated with a surface modifier to inhibit the aggregation of the particles. One or more other excipients can be added either to the active agent or to the aqueous medium.

EXAMPLE 1

Preparation of 1% Itraconazole Suspension with Deoxycholic Acid Coating

Each 100 mL of suspension contains:

| | |
|---|---|
| Itraconazole | 1.0 g (1.0% w/v) |
| Deoxycholic Acid, Sodium Salt, Monohydrate | 0.1 g (0.1% w/v) |
| Poloxamer 188, NF | 0.1 g (0.1% w/v) |
| Glycerin, USP | 2.2 g (2.2% w/v) |
| Sodium Hydroxide, NF (0.1 N or 1.0 N) | for pH Adjustment |
| Hydrochloric Acid, NF (0.1 N or 1.0 N) | for pH Adjustment |
| Sterile Water for Injection, USP | QS |
| Target pH (range) | 8.0 (6 to 9) |

Preparation of Surfactant Solution (2 Liters) for Microprecipitation

Fill a properly cleaned tank with Sterile Water for Injection and agitate. Add the required amount of glycerin and stir until dissolution. Add the required amount of deoxycholic acid, sodium salt monohydrate and agitate until dissolution. If necessary, adjust the pH of the surfactant solution with minimum amount of sodium hydroxide and/or hydrochloric acid to a pH of 8.0. Filter the surfactant solution through a 0.2 µm filter. Quantitatively transfer the surfactant solution to the vessel supplying the homogenizer. Chill the surfactant solution in the hopper with mixing.

Preparation of Replacement Solution

Preparation of 4 liters of replacement solution. Fill a properly cleaned tank with WFI and agitate. Add the weighed Poloxamer 188 (Spectrum Chemical) to the measured volume of water. Begin mixing the Poloxamer 188/water mixture until the Poloxamer 188 has completely dissolved. Add the required amount of glycerin and agitate until dissolved. Once the glycerin has completely dissolved, add the required amount of deoxycholic acid, sodium salt monohydrate and stir until dissolution. If necessary, adjust the pH of the wash solution with the minimum amount sodium hydroxide and/or hydrochloric acid to a pH of 8.0. Filter the replacement solution through a 0.2 µm membrane filter.

Preparation of Drug Concentrate

For a 2-L batch, add 120.0 mL of N-methyl-2-pyrrolidinone into a 250-mL beaker. Weigh 2.0 g Poloxamer 188. Weigh 20.0 g of itraconazole (Wyckoff). Transfer the weighed Poloxamer 188 to the 250 mL beaker with N-methyl-2-pyrrolidinone. Stir until dissolved, then add the itraconazole. Heat and stir until dissolved. Cool the drug concentrate to room temperature and filter through a 0.2-micron filter.

Microprecipitation

Add sufficient WFI to the surfactant solution already in the vessel supplying the homogenizer so that the desired target concentration is reached. When the surfactant solution is cooled, start adding the drug concentrate into the surfactant solution with continuous mixing.

Homogenization

Slowly increase the pressure of the homogenizer until the operating pressure 10,000 psi has been reached. Homogenize the suspension with recirculation while mixing. For 2,000 mL of suspension at 50 Hz, one pass should require approximately 54 seconds. Following homogenization, collect a 20-mL sample for particle size analysis. Cool the suspension.

Wash Replacement

The suspension is then divided and filled into 500-mL centrifuge bottles. Centrifuge until clean separation of sediment is observed. Measure the volume of supernatant and replace with fresh replacement solution, prepared earlier. Quantitatively transfer the precipitate from each centrifuge bottle into a properly cleaned and labeled container for resuspension (pooled sample). Resuspension of the pooled sample is performed with a high shear mixer until no visible clumps are observed. Collect a 20-mL sample for particle size analysis.

The suspension is then divided and filled into 500-mL centrifuge bottles. Centrifuge until clean separation of sediment is observed. Measure the volume of supernatant and replace with fresh replacement solution, prepared earlier. Quantitatively transfer the precipitate from each centrifuge bottle into a properly cleaned and labeled container for resuspension (pooled sample). Resuspension of the pooled sample is performed with a high shear mixer until no visible clumps are observed. Collect a 20-mL sample for particle size analysis.

Second Homogenization

Transfer the above suspension to the hopper of the homogenizer and chill the suspension with mixing. Slowly increase the homogenizer pressure until an operating pressure 10,000 psi has been reached. Homogenize while monitoring the solution temperature. Following homogenization, cool the suspension and collect three 30-mL samples for particle analysis. Collect the remaining suspension in a 2-liter bottle.

Filling

Based on acceptable particle size determination testing (mean volume-weighted diameter of 50 nm to 5 microns), collect 30 mL samples in 50 mL glass vials with rubber stoppers.

EXAMPLE 2

Preparation of 1% Itraconazole Nanosuspension with Phospholipid Coating

Each 100 mL of suspension contains:

| | |
|---|---|
| Itraconazole | 1.0 g (1.0% w/v) |
| Phospholipids (Lipoid E 80) | 1.2 g (1.2% w/v) |
| Glycerin, USP | 2.2 g (2.2% w/v) |
| Sodium Hydroxide, NF (0.1 N or 1.0 N) | for pH Adjustment |
| Hydrochloric Acid, NF (0.1 N or 1.0 N) | for pH Adjustment |
| Sterile Water for Injection, USP | QS |
| Target pH (range) | 8.0 (7.5 to 8.5) |

Preparation of Surfactant Solution (2 Liters) for Microprecipitation

The surfactant solution is prepared in two phases. Phase 1 is dispersed phospholipids, whereas Phase 2 includes filtered glycerin. The two fractions are combined prior to pH adjustment.

Phase 1: Fill a properly cleaned vessel with approximately 700 mL of Sterile Water for Injection, USP (WFI) with agitation at 50-500 rpm. Increase the temperature of the filtrate to 50° C.-70° C. and add the required amount of phospholipids with mixing at 50-500 rpm until complete dispersion is achieved. Document the time and temperature at which the phospholipids were added and at which it was dispersed. Determine the total mixing time required to disperse the phospholipids. Cool the surfactant solution to 18° C.-30° C. prior to the addition of glycerin.

Phase 2: Fill a properly cleaned vessel with approximately 700 mL of WFI with agitation at 50-500 rpm. Add the required amount of glycerin at 18° C.-30° C. and agitate at 50-500 rpm until dissolution.

Combined Phases: Filter the glycerin solution through a 0.2 µm filter set-up into Phase 1 (at 18° C.-30° C.) while mixing at 50-500 rpm. Volume is approximately 1.4 liters. Record the pH of the surfactant solution. If necessary, adjust the pH of the surfactant solution with a minimum amount of sodium hydroxide and/or hydrochloric acid to a pH of 8.0±0.5. Measure the volume of the surfactant solution at 18° C.-30° C. using a 2-L graduated cylinder.

Quantitatively transfer the surfactant solution to the vessel supplying the homogenizer (Avestin C-160). Chill the surfactant solution in the hopper with mixing at a speed with an observable solution vortex until the temperature is not more than 10° C.

Preparation of Replacement Solution (4 L)

The replacement solution is prepared in two phases. Phase 1 includes dispersed phospholipids, whereas Phase 2 includes filtered glycerin. The two fractions are combined prior to pH adjustment.

Phase 1: Fill a properly cleaned vessel with approximately 1.4 liters of WFI with agitation at 50-500 rpm. Increase the temperature of the water to 50° C.-70° C. and add the required amount of phospholipids with mixing at 50-500 rpm until complete dispersion is achieved. Cool the surfactant solution to 18° C.-30° C. prior to the addition of glycerin.

Phase 2: Fill a properly cleaned vessel with approximately 1.4 L of WFI with agitation at 50-500 rpm. Add the required amount of glycerin and agitate at 50-500 rpm until dissolution.

Combined Phases: Filter the glycerin solution through a 0.2 µm filter set-up into Phase 1 (at 18° C.-30° C.) while mixing at 50-500 rpm. Dilute to volume with Water for Injection to 4.0 L using a graduated cylinder. Record the pH of the wash solution. If necessary, adjust the pH of the wash solution with the minimum amount sodium hydroxide and/or hydrochloric acid to a pH of 8.0±0.5.

Preparation of Drug Concentrate

For a 2-L batch, add 120.0 mL of N-methyl-2-pyrrolidinone (Pharmasolve®, ISP) into a 250-mL beaker. Weigh 20.0 g of itraconazole (Wyckoff). Transfer the weighed itraconazole to the 250-mL beaker with NMP at NMT 70° C. Maintain below 70° C. and stir at 100-1000 rpm until dissolved. Cool the drug concentrate to 18° C.-30° C. Filter the drug concentrate through a prefilter and filter set-up. Use one polypropylene prefilter SBPP and two 0.2 µm filters at 15 psi and ambient temperature. Transfer the drug concentrate to three 60-mL syringes and attach syringe needles to the luer connections of the syringes. Using the syringes, determine the volume of drug concentrate.

Microprecipitation

Add Water for Injection to the surfactant solution already in the vessel supplying the homogenizer. The amount of water at 18° C.-30° C. added should be calculated as:

$$V = 2{,}000 \text{ mL} - \text{Volume of Drug Concentrate} - \text{Volume of Surfactant Solution}$$

Mount each syringe needle assembly using a syringe pump. Position the outlet of the needle on top of the vessel. When the surfactant solution is not more than 10° C., start adding the drug concentrate into the surfactant solution with continuous mixing at a speed needed to create a distinctive solution vortex. The concentrate should be added so that the drops hit the point of highest shear, at the bottom of the vortex. The rate of addition should be approximately 2.5 mL/min.

Homogenization

An Avestin C160 homogenizer was used. Slowly increase the pressure of the homogenizer until the operating pressure 10,000 psi has been reached. Homogenize the suspension for 20 passes (18 minutes) with recirculation while mixing at 100-300 rpm and maintaining the suspension temperature below 70° C. For 2,000 mL of suspension at 50 Hz, one pass requires approximately 54 seconds. Following homogenization, collect a 20 mL sample in a 50 mL glass vial for particle size analysis. Cool the suspension to not more than 10° C.

Wash Replacement

The suspension is then divided and filled into 500-mL centrifuge bottles. Set the speed for the centrifuge at 11,000 rpm using the rotor SLA-3000, Superlite equivalent to approximately 20,434 g. The total centrifuge time is 60 min at not more than 10° C. Measure the volume of supernatant and replace with fresh replacement solution. Using spatula(s), quantitatively transfer the precipitant from each centrifuge bottle into a properly cleaned and labeled container for resuspension (pooled sample). Resuspension of the pooled sample is performed with a high shear mixing until no visible clumps are observed.

Second Washing and Centrifuging Step

The suspension is then divided and filled into 500-mL centrifuge bottles. Set the speed for the centrifuge at 11,000 rpm using the rotor SLA-3000, Superlite equivalent to approximately 20,434 g. The total centrifuge time is 60 min at not more than 10° C. Measure the volume of supernatant and replace with fresh replacement solution. Using spatula(s), quantitatively transfer the precipitant from each centrifuge bottle into a properly cleaned and labeled container for resuspension (pooled sample). Resuspension of the pooled sample is performed under high-shear mixing until no visible clumps are observed. Record the pH of the suspension. If necessary, adjust the pH of the suspension with the minimum amount sodium hydroxide and/or hydrochloric acid to a pH of 8.0±0.5.

Second Homogenization

Transfer the above suspension to the hopper of the homogenizer. Chill the suspension with mixing until the temperature is less than 10° C. Slowly increase the pressure until an operating pressure of 10,000 psi has been reached. Homogenize for 20 passes (18 minutes) while maintaining the solution temperature below 70° C. Following homogenization, cool the suspension to less than 10° C. and collect three 30-mL samples for particle-size analysis. Collect the remaining suspension in a 2-liter bottle. Sparge the suspension with nitrogen gas for 10 min. Ensure the nitrogen gas is filtered through a 0.2 µm filter.

Filling

Based on acceptable particle size determination testing (mean volume-weighted diameter of 50 to 1000 nm), collect 30-mL samples in 50-mL glass vials with PTFE®-coated stoppers. Purge the headspace of each vial with nitrogen prior to sealing.

EXAMPLE 3

Other Formulations of Itraconazole Suspensions

Other formulations of itraconazole suspensions with different combinations of the surfactants can also be prepared using the method described in Example 1 or Example 2. Table 1 summarizes the compositions of the surfactants of the various itraconazole suspensions.

TABLE 1

Summary of the compositions of the various 1% itraconazole suspensions

| Formulation No. | Surfactants in the formulation | Amount* |
|---|---|---|
| 1 | Poloxamer 188 | 0.1% |
|   | Deoxycholate | 0.1% |
|   | Glycerin | 2.2% |
| 2 | Poloxamer 188 | 0.1% |
|   | Deoxycholate | 0.5% |
|   | Glycerin | 2.2% |
| 3 | Poloxamer 188 | 2.2% |
|   | Deoxycholate | 0.1% |
|   | Glycerin | 2.2% |
| 4 | Poloxamer 188 | 2.2% |
|   | Deoxycholate | 0.5% |
|   | Glycerin | 2.2% |
| 9 | Solutol | 0.3% |
|   | Deoxycholate | 0.5% |
|   | Glycerin | 2.2% |
| 14331-1 | Solutol | 1.5% |
|   | Glycerin | 2.2% |
| 14443-1 | Albumin | 5% |
| 14 | Phospholipid | 2.2% |
|   | Deoxycholate | 0.5% |
|   | Glycerin | 2.2% |
|   | $Na_2PO_4$ | 0.14% |
| A6 | Phospholipid | 1.2% |
|   | Glycerin | 2.2% |
| B | Phospholipid | 1.2% |
|   | Glycerin | 2.2% |
|   | N-methyl-2-pyrrolidinone | trace |
| C | Phospholipid | 1.2% |
|   | Glycerin | 2.2% |
|   | Lactic acid | trace |
| 14412-3 | Phospholipid | 1.2% |
|   | Hydroxyethyl starch | 1.0% |
|   | Glycerin | 2.2% |
|   | TRIS | 0.06% |

*% by weight of the final volume of the suspension (w/v)

EXAMPLE 4

Comparison of the Acute Toxicity Between Commercially Available Itraconazole Formulation (SPORANOX®) and the Suspension Compositions of the Present Invention The acute toxicity of the commercially available itraconazole formulation (SPORANOX®) is compared to that of the various 1% itraconazole formulations in the present invention as listed in Table 1. SPORANOX® is available from Janssen Pharmaceutical Products, L.P. It is available as a 1% intravenous (I.V.) solution solubilized by hydroxypropyl-β-cyclodextrin. The results are shown in Table 2 with the maximum tolerated dose (MTD) indicated for each formulation.

TABLE 2

Comparison of the acute toxicity of various formulations of itraconazole

| Formulation Number | Results and Conclusions |
|---|---|
| SPORANOX ® I.V. | $LD_{10}$ = 30 mg/kg |
|   | MTD = 20 mg/kg (slight ataxia) |
| 1 | MTD = 320 mg/kg; NOEL = 80 mg/kg |
|   | Spleen obs[b]: 320 mg/kg |
|   | Red ears/feet: ≧160 mg/kg |
| 2 | MTD = 320 mg/kg |
|   | Spleen obs[b]: 320 mg/kg |
|   | Slight lethargy: 320 mg/kg |
|   | Red urine: ≧80 mg/kg |
|   | Tail obs[c]: ≧40 mg/kg |
| 3 | MTD = 160 mg/kg; NOEL = 80 mg/kg |
|   | Spleen obs[b]: 320 mg/kg |
|   | Red ears/feet: ≧160 mg/kg |
| 4 | MTD = 160 mg/kg |
|   | $LD_{20}$ = 320 mg/kg |
|   | Spleen obs[b]: 320 mg/kg |
|   | Slight lethargy: 320 mg/kg |
|   | Red urine: ≧40 mg/kg |
|   | Tail obs[c]: ≧40 mg/kg |
| 9 | $LD_{60}$ = 320 mg/kg; MTD = 160 mg/kg |
|   | Spleen obs[b]: 320 mg/kg |
|   | Tail obs: 320 mg/kg |
|   | Red ears/feet: ≧160 mg/kg |
|   | Red urine: ≧40 mg/kg |
| 14331-1 | MTD = 40 mg/kg; NOEL = 40 mg/kg |
|   | $LD_{40}$ = 80 mg/kg |
| 14443-1 | $LD_{40}$ = 80 mg/kg; NOEL = 40 mg/kg |
| 14 | MTD = 320 mg/kg; NOEL = 40-80 mg/kg |
|   | Spleen obs[b]: 320 mg/kg |
|   | Ataxia = 320 mg/kg |
|   | Tail obs = 320 mg/kg |
| A6 | MTD = 320 mg/kg; NOEL = 160 mg/kg |
|   | Spleen obs[b]: 320 mg/kg |
| B | MTD = 320 mg/kg; NOEL = 80 mg/kg |
|   | Spleen obs[b]: 160 mg/kg |
|   | Red ears/feet: ≧160 mg/kg |
| C | MTD = 320 mg/kg; NOEL = 80 mg/kg |
|   | Spleen obs[b]: ≧160 mg/kg |
|   | Red ears/feet: ≧160 mg/kg |
| 14412-3 | MTD = 320 mg/kg; NOEL = 80 mg/kg |
|   | Spleen obs[b]: ≧160 mg/kg |

[a]cyclodextrin = hydroxypropyl-β-cyclodextrin
[b]Spleen obs = Enlarged and/or pale
[c]Tail obs = gray to black and/or necrosis
$LD_{10}$ = Lethal dose resulting in 10% mortality
$LD_{40}$ = Lethal dose resulting in 40% mortality
$LD_{50}$ = Lethal dose resulting in 50% mortality
NOEL = No effect level
MTD = Maximum tolerated dose The data in Table 2 indicated that the animals tolerated a much higher level of the antifungal agent itraconazole when formulated in a nanosuspension than when formulated as a solution with cyclodextrin. It may be thought that the reason for the increased tolerability is associated with not using cyclodextrin. However, cyclodextrin, by itself, at the levels used in Sporanox would not cause the degree of toxicity observed. Rather, it is believe, the reason lies in alteration of the pharmacokinetic profile caused by the nanosuspension.

EXAMPLE 5

Pharmacokinetic Comparison of SPORANOX® Vs. Suspension Formulation of Itraconazole Young adult, male Sprague Dawley rats were treated intravenously (IV) via a caudal tail vein with a single injection at a rate of 1 mL/min. with either SPORANOX® Injection, or Formulations 1 and B at 20, 40, and 80 mg/kg, or Formulations 3, 14, A6 and C at 80 mg/kg.

Following administration, the animals were anesthetized and retro-orbital blood was collected at different time points (n=3). The time points were as follows: 0.03, 0.25, 0.5, 1, 2, 4, 6, 8, 24, 48, 96, 144, 192, 288, and 360 hours (SPORANOX® Injection only to 192 hours). Blood was collected into tubes with EDTA and centrifuged at 3200 rpm for 15 minutes to separate plasma. The plasma was stored frozen at −70° C. until analysis. The concentration of the parent itraconazole and the metabolite hydroxy-itraconazole were determined by high-performance liquid chromatography (HPLC). Pharmacokinetic (PK) parameters for itraconazole (ITC) and hydroxy-itraconazole (OH-ITC) were derived using noncompartmental methods with WinNonlin® Professional Version 3.1 (Pharsight Corp., Mountain View, Calif.).

Table 3 provides a comparison of the plasma pharmacokinetic parameters determined for each itraconazole formulation. Plasma itraconazole was no longer detected at 24 hours for SPORANOX® Injection at 5 mg/kg, at 48 hours for SPORANOX® Injection at 20 mg/kg, and at 96 hours for Formulations 1 and B. Plasma hydroxy-itraconazole was initially detected at 0.25 hours for SPORANOX® Injection and Formulations 1 and B. Plasma hydroxy-itraconazole was initially detected at 0.25 hours for SPORANOX® Injection at 5 and 20 mg/kg and Formulations 1 and; B at 20 mg/kg, Hydroxy-itraconazole was no longer detected at 48 hours for SPORANOX® Injection at 5 mg/kg, at 96 hours for SPORANOX® Injection at 20 mg/kg, and at 144 hours for Formulations 1 and B.

metabolized effectively, as is shown by the PK curve for the hydroxy itraconazole metabolite. The rate of appearance of the metabolite for the nanosuspension is delayed, compared with the PK curve for the metabolite for the SPORANOX® formulation. However, as with the case of the parent molecule for the nanosuspension, the metabolite Persists in circulation for a much longer time than is the case with the metabolite for the SPORANOX® formulation. When the AUC (area under the blood concentration vs time curve) is normalized by the dose, the nanosuspension is at least as bioavailable as SPORANOX®.

EXAMPLE 6

Acute Toxicity of Fast Dissolving Nanosuspensions

Additional experiments were performed. Itraconazole nanosuspensions were formulated differently, so as to dissolve much more readily in blood. This was accomplished by making the particles either smaller or amorphous, or both. These acute toxicity of these formulations is described for formulation entries 14331-1 and 14443-1 in Table 1. In contrast to the slowly dissolving nanosuspensions, the fast dissolving nanosuspension caused death in the animals at much lower levels, similar to what was found with SPORANOX®. Since these fast dissolving nanosuspensions did not contain cyclodextrin, it is clear that this excipient was not responsible for the toxicity. Rather the rapid dissolution, resulting in

TABLE 3

Comparison of Plasma Pharmacokinetic Parameters for Sporanox and a Suspension Formulation After IV Administration in Rats

| Analyte | PK Parameters | 5 mg/kg Spor | 20 mg/kg Spor | 20 mg/kg 1 | 20 mg/kg B | 40 mg/kg 1 | 40 mg/kg B | 80 mg/kg 1 | 80 mg/kg B | 80 mg/kg A6 | 80 mg/kg C | 80 mg/kg 3 | 80 mg/kg 14 |
|---|---|---|---|---|---|---|---|---|---|---|---|---|---|
| Itraconazole | C max (ug/ml) | 2.42 | 13.12 | 30.41 | 9.10 | 119.16 | 10.20 | 446.33 | 15.20 | 39.72 | 53.19 | 365.09 | 68.15 |
| | T max (h) | 0.03 | 0.03 | 0.03 | 0.03 | 0.03 | 0.03 | 0.03 | 0.03 | 0.03 | 0.03 | 0.03 | 0.03 |
| | AUC (0-∞) (ug·h/ml) | 3.90 | 28.25 | 16.70 | 15.79 | 42.67 | 36.11 | 143.70 | 80.31 | 58.71 | 94.19 | 108.87 | 85.53 |
| | $T_{1/2}$ (h) | 2.75 | 5.36 | 14.36 | 14.54 | 23.95 | 20.49 | 25.89 | 28.63 | 54.02 | 33.75 | 38.46 | 31.17 |
| | CL (ul/h) | 320.17 | 176.97 | 299.35 | 316.67 | 234.38 | 276.90 | 139.18 | 249.04 | 340.64 | 212.33 | 183.71 | 233.83 |
| | MRT (h) | 2.57 | 4.48 | 13.29 | 15.32 | 24.37 | 28.76 | 27.45 | 52.84 | 58.21 | 46.85 | 31.21 | 41.93 |
| Hydroxy-Itraconazole | Cmax (ug/ml) | 0.38 | 0.78 | 0.40 | 0.44 | 0.61 | 0.69 | 1.03 | 0.48 | 0.32 | 0.56 | 0.52 | 0.51 |
| | T max (h) | 4.04 | 4.0 | 24 | 8 | 24 | 24 | 24 | 48 | 48 | 24.0 | 24.0 | 24.0 |
| | AUC (0-∞) (ug·h/ml) | 3.96 | 13.41 | 17.89 | 20.71 | 37.71 | 44.69 | 70.24 | 56.01 | 47.27 | 59.40 | 51.27 | 51.89 |
| | $T_{1/2}$ (h) | 7.98 | 5.89 | 15.50 | 18.06 | 22.27 | 28.12 | 23.21 | 36.45 | 60.87 | 38.84 | 50.29 | 25.50 |
| | MRT (h) | 7.55 | 12.17 | 30.99 | 29.23 | 43.06 | 36.02 | 46.80 | 68.35 | 74.88 | 65.71 | 60.81 | 58.02 |

Figure 5:
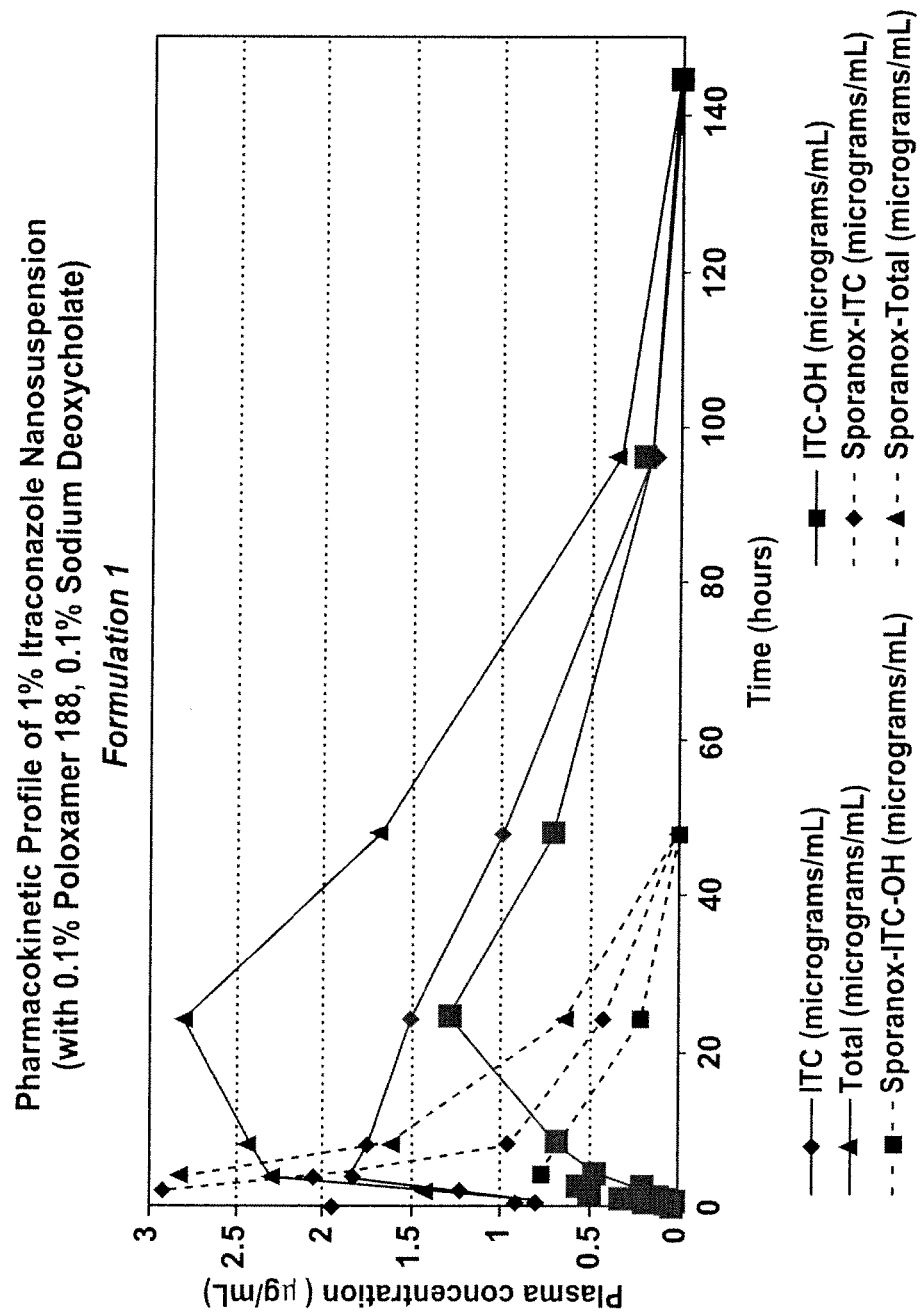
FIG. 5 is a graph comparing the pharmacokinetics of SPORANOX® with Formulation 1 suspension of itraconazole of the present invention, wherein ITC=plasma concentration of itraconazole measured after bolus injection of Formulation 1 (80 mg/kg), ITC-OH=plasma concentration of primary metabolite, hydroxyitraconazole, measured after bolus injection of Formulation 1 (80 mg/kg), Total=combined concentration of itraconazole and hydroxyitraconazole (ITC+ITC-OH) measured after bolus injection of Formulation 1 (80 g/kg), Sporanox–ITC=plasma concentration of itraconazole measured after bolus injection of 20 mg/kg Sporanox IV, Sporanox–ITC-OH=plasma concentration of primary metabolite, hydroxyitraconazole, measured after bolus injection of 20 mg/kg Sporanox IV, Sporanox–Total=combined concentration of itraconazole and hydroxyitraconazole (ITC+ITC-OH) measured after bolus injection of 20 mg/kg Sporanox IV.
Figure 6:
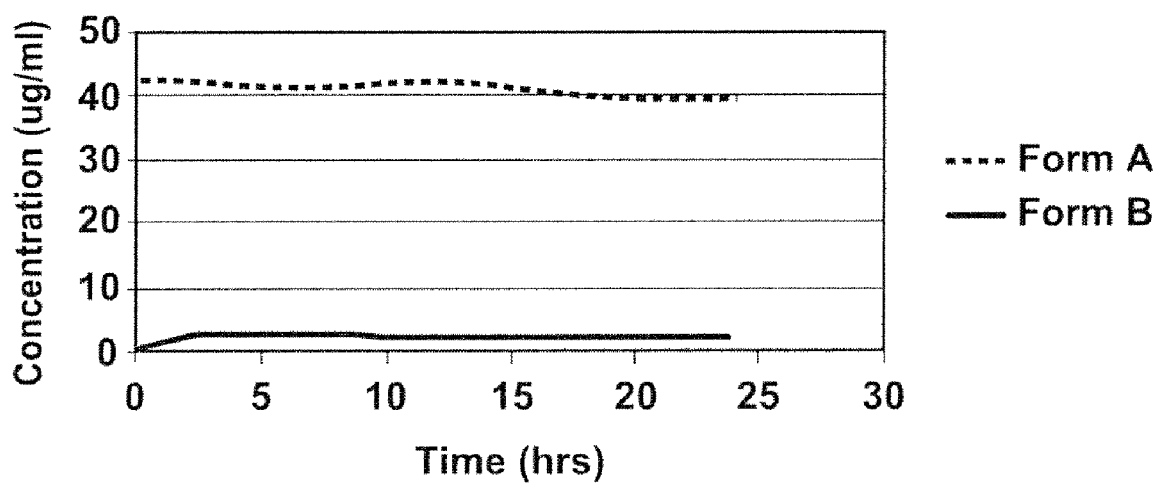
FIG. 6 is a graph comparing the drug level for the rapidly dissolving formulation, Form A, and the slow dissolving (macrophage targeting) formulation, Form B, as determined in an in vitro dissolution experiment; the drug level for Form A is much higher than that attained by Form B.

FIG. 5 compares the pharmacokinetics (PK) of SPORANOX® with Formulation 1 suspension of itraconazole particles. Because, as shown above, the present suspension formulation is less toxic than Sporanox®, it was administered at higher amounts in this equitoxic experiment. Sporanox was dosed at 20 mg/kg and Formulation 1 at 80 mg/kg. The SPORANOX® decreases in plasma concentration relatively quickly, over 20 hours. The nanosuspension plasma levels remain elevated for approximately 3-4 times longer. The nanosuspension exhibits an initial minimum at 30 minutes in the plasma level. This corresponds to a nadir in plasma concentration due to sequestration of the drug nanocrystals by the macrophages of the spleen and liver, thus temporarily removing drug from circulation. However, the drug levels rebound quickly, as the macrophages apparently release the drug into the circulation. Furthermore, the nanosuspension drug is immediate availability of the drug in the blood was the causative factor. The drug level for the rapidly dissolving formulation, Form A, is much higher than that attained by the slow dissolving (macrophage targeting) formulation, Form B, as determined in an in vitro dissolution experiment. This involved a plasma simulating media consisting of 5% albumin/Sorenson's buffer. Results are shown in FIG. 6.

EXAMPLE 7

Antifungal Efficacy Studies

Normal and immuno-suppressed (prednisolone administered twice daily on the day before and on the day of inoculation) rats inoculated with $9.5 \times 10^6$ or $3 \times 10^6$ cfu C. albicans/ml saline once intravenously were intravenously treated with SPORANOX® Injection once daily for ten consecutive days, with the first dose given 4 to 5 hours after inoculation. SPORANOX® Injection rats were dosed at 5 or 20 mg/kg for the first 2 days, then at 5 or 10 mg/kg for the remaining 8 days, due to toxicity at 20 mg/kg after 2 days of dosing. Similarly, immuno-suppressed rats inoculated with $1 \times 10^{6.5}$ cfu C. albicans/ml saline were intravenously treated with Formulation 1 or B each at 20, 40, or 80 mg/kg once every other day for ten days, beginning the day of inoculation. The SPORANOX® Injection, Formulation 1, and Formulation B treatment rats were terminated 11 days after the C. albicans inoculation and the kidneys were collected, weighed and cultured for determination of C. albicans colony counts and itraconazole and hydroxy-itraconazole concentration. Kidneys were collected from untreated control rats when a moribund condition was observed or when an animal had a 20% body weight. In addition, body weights were measured periodically during the course of each study.

Figure 7A:
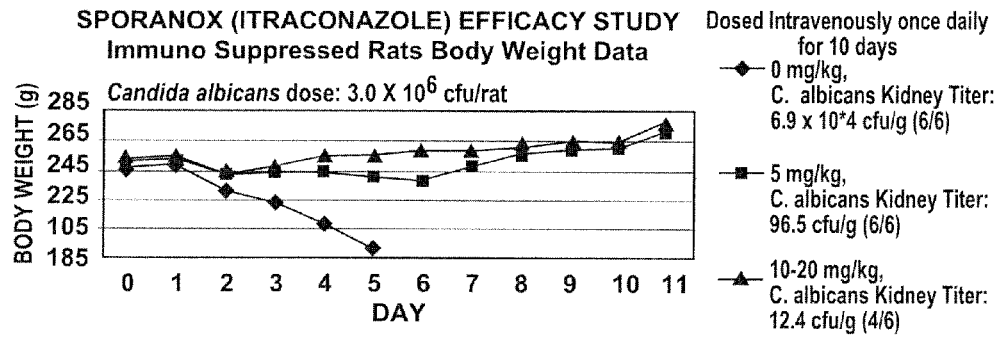
FIGS. 7A, 7B, and 7C are graphs showing the comparison of results for body weight over time for immuno-suppressed rats treated with SPORANOX® injection (FIG. 7A) and Formulations 14288-1 (FIG. 7B) and 14288-B (FIG. 7C)
Figure 7B:
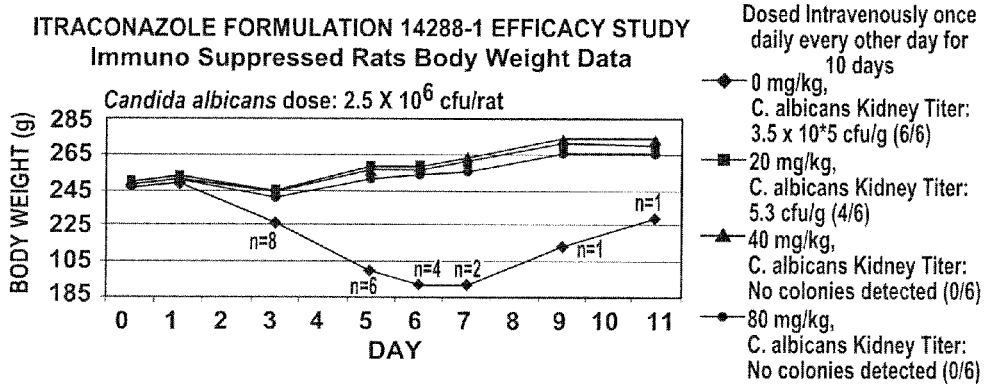
Figure 7C:
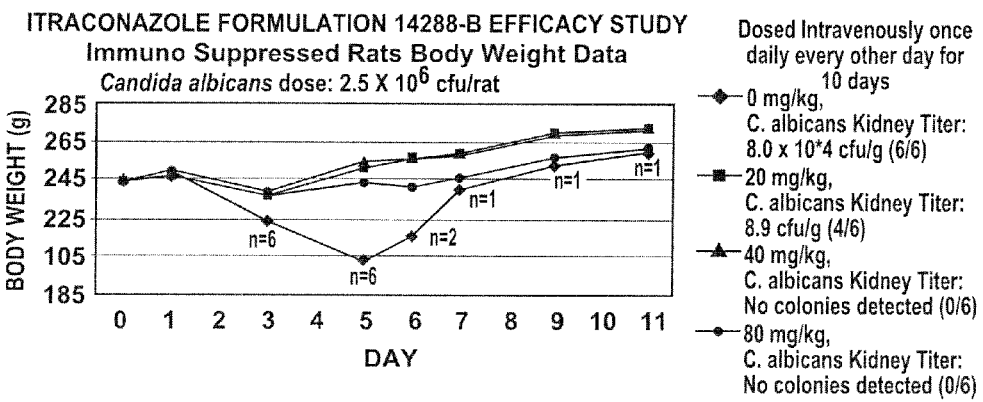

Comparison of results for immuno-suppressed rats treated with SPORANOX® Injection and Formulations 1 and B are shown in Table 4 and FIG. 7. Daily SPORANOX® Injection treatment at 10-20 mg/kg appeared to be slightly more effective than daily treatment with SPORANOX® Injection at 5 mg/kg. Based on kidney colony counts, every other day dosing at 20 mg/kg of Formulation 1 or B appeared to be as effective as every day dosing with SPORANOX® Injection at 20 mg/kg and possibly more effective than SPORANOX® Injection at 5 mg/kg (i.e., the recommended clinical dose), whereas the higher doses for both Formulation 1 and B appeared to most effective, based on kidney colony counts (i.e., C. albicans not detected) and increased kidney itraconazole concentration.

EXAMPLE 8

Resistant Strain Anti-Fungal Efficacy Test

A lethal dose of a C. albicans strain c43 (ATCC number 201794) ($MIC_{80}$=16 µg/ml for SPORANOX® itraconazole; 8-16 for Vfend, and 0.1 for Cancidas) was administered to an immunocompromised rat model (prednisolone qd). 24 h later, test groups (n=6) were treated q2d with 20, 40, or 80 mg/kg NANOEDGE™ itraconazole nanosuspension. Control groups included a no treatment arm, Sporanox® (10 mg/kg/d), Vfend® (10 mg/kg/d), and Cancidas® (1 mg/kg/d). Treatment was continued for 10 days. Survival and kidney cfu/g were assessed.

Figure 10:
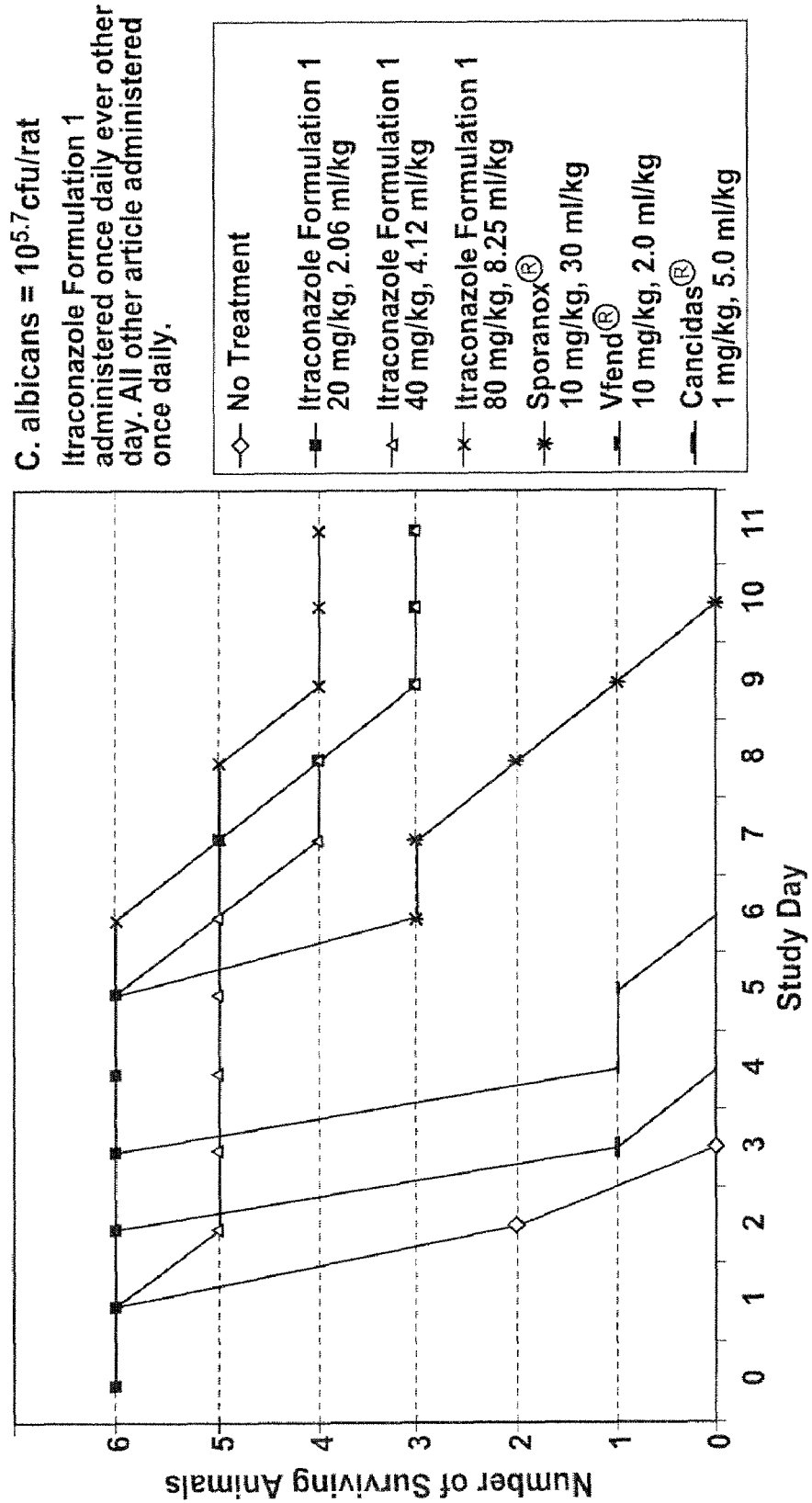
FIG. 10 is a graph showing the mortality/moribundity profile after daily or every other day dosing with antifungal drugs for 10 days in rats systemically infected with itraconazole resistant *C. albicans*.

The number of surviving animals after 6 and 10 days, were respectively: Sporanox (3.0), 20 and 40 mg/kg nanosuspension (5.3), 80 mg/kg nanosuspension (6.4), Vfend (0.0), Cancidas (0.0). FIG. 10.

It can be concluded that the greater dosing possible with the itraconazole nanosuspension can effectively treat infections of C. albicans strains, conventionally assumed to be resistant to itraconazole, resulting in increased survival in an immunocompromised rat model.

Current definitions of sensitive and resistant fungal strains presume a specified dose of itraconazole that is administered, using conventional dosage forms. Greater drug loading, attendant with nanosuspension injections, may permit treatment of what are currently considered itraconazole-resistant C. albicans infections.

TABLE 4

Mean C. albicans Colony Count and Itraconazole and Hydroxy-Itraconazole Concentration in Kidney

| | C. albicans Titer | | Concentration in Kidney | |
| --- | --- | --- | --- | --- |
| Treatment | Count (cfu/g) | Incidence | ITC (µg/g) | OH-ITC (µg/g) |
| No Treatment ($3 \times 10^6$ cfu/ml) | $6.9 \times 10^4$ | 6/6 | — | — |
| SPORANOX ®, 5 mg/kg, ($3 \times 10^6$ cfu/ml) | 96.5 | 6/6 | 1.2 | 1.5 |
| SPORANOX ®, 10-20 mg/kg, ($3 \times 10^6$ cfu/ml) | 12.4 | 4/6 | 8.5 | 8.0 |
| No Treatment ($2.5 \times 10^6$ cfu/ml) | $3.5 \times 10^5$ | 6/6 | — | — |
| Formulation 1, 20 mg/kg, ($2.5 \times 10^6$ cfu/ml) | 5.3 | 4/6 | 6.1 | 5.7 |
| Formulation 1, 40 mg/kg, ($2.5 \times 10^6$ cfu/ml) | 0 | 0/6 | 18.5 | 6.0 |
| Formulation 1, 80 mg/kg, ($2.5 \times 10^6$ cfu/ml) | 0 | 0/6 | 41.2 | 6.2 |
| No Treatment ($2.5 \times 10^6$ cfu/ml) | $8.0 \times 10^4$ | 6/6 | — | — |
| Formulation B, 20 mg/kg, ($2.5 \times 10^6$ cfu/ml) | 8.9 | 4/6 | 2.5 | 2.5 |
| Formulation B, 40 mg/kg, ($2.5 \times 10^6$ cfu/ml) | 0 | 0/6 | 7.8 | 4.0 |
| Formulation B, 80 mg/kg, ($2.5 \times 10^6$ cfu/ml) | 0 | 0/6 | 21.3 | 4.6 |

Figure 8:
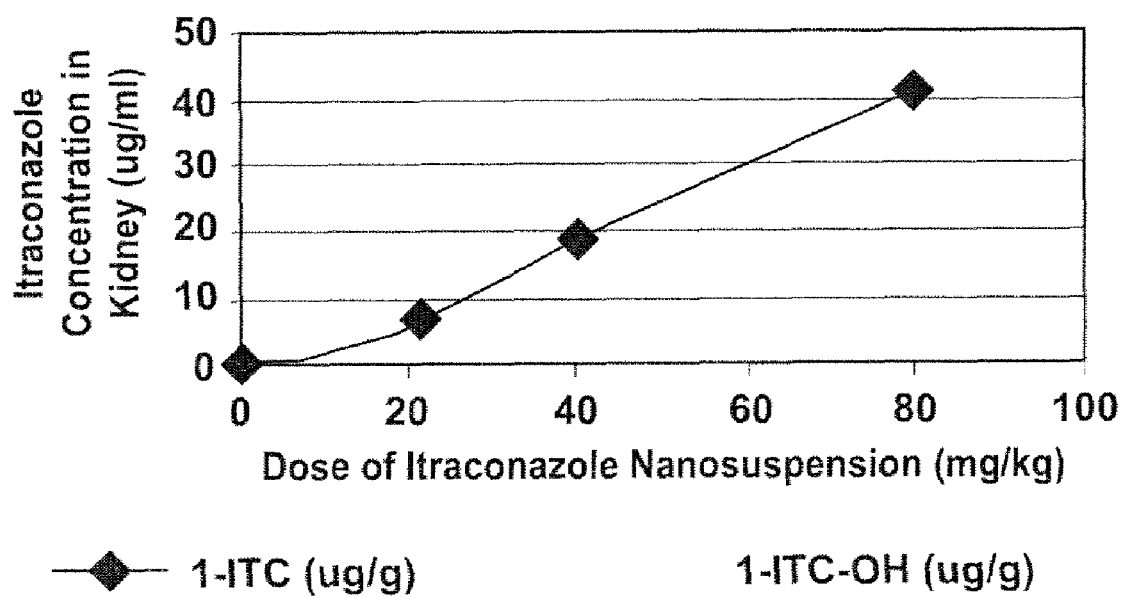
FIG. 8 is a graph of kidney drug level vs. dose showing that the greater dosing that could be administered permitted greater drug levels to be manifested in the target organs, in this case, the kidney.
Figure 9:
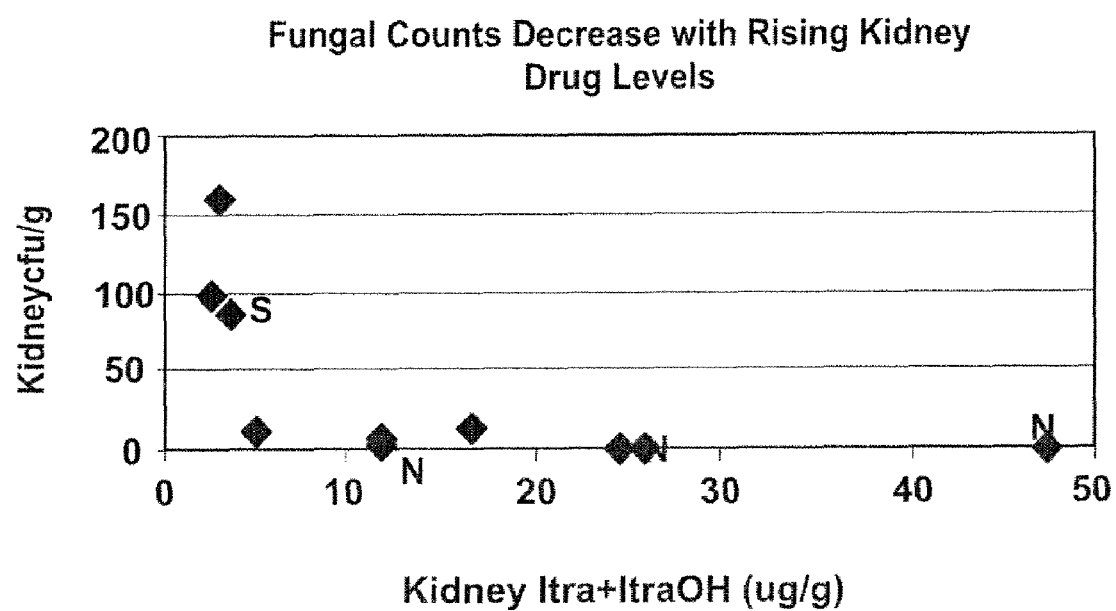
FIG. 9 is a graph of fungal counts vs. kidney drug level (N=nanosuspension; S=Sporanox IV solution) showing that the greater drug levels in the target organ (the kidney) led to a greater kill of the infectious organisms.

In the examples above, a nanosuspension formulation of an anti-fungal agent was shown to be less toxic than a conventional totally soluble formulation of the same drug. Thus, more of the drug could be administered without eliciting adverse effects. Because the nanoparticles of the drug did not immediately dissolve upon injection, they were trapped in a depot store in the liver and spleen. These acted as prolonged release sanctuaries, permitting less frequent dosing. The greater dosing that could be administered permitted greater drug levels to be manifested in the target organs, in this case, the kidney (FIG. 8). The greater drug levels in this organ led to a greater kill of infectious organisms. (FIG. 9).

EXAMPLE 9

Prophetic Examples of Other Triazole Antifungal Agents

The present invention contemplates preparing a 1% suspension of submicron- or micron size of a triazole anti fungal agent using the method described in Example 1 or Example 2 and the formulations described in Example 3 with the exception that the antifungal agent is a triazole antifungal agent other than itraconazole. Examples of triazole antifungal agents that can be used include, but are not limited to, ketoconazole, miconazole, fluconazole, ravuconazole, vericonazole, saperconazole, eberconazole, genaconazole, clotrimazole, econazole, oxiconazole, sulconazole, terconazole, tioconazole, and posaconazole.

EXAMPLE 10

Prophetic Example of a Non-Triazole Antifungal Agent

The present invention contemplates preparing a 1% suspension of submicron- or micron size non-triazole antifungal agent using the method described in Example 1 or Example 2 and the formulations described in Example 3 with the exception that the antifungal agent is amphotericin B, nystatin, terbinafine, anidulafungin, or flucytosine instead of itraconazole.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. A method for treating a subject infected with *Candida albicans* strain c43, the method comprising the step of administering itraconazole to a subject infected with *Candida albicans* strain c43, wherein the *Candida albicans* strain c43 has a MIC greater than 8 µg/mL for itraconazole, wherein the itraconazole is formulated as an aqueous suspension of submicron- to micron-size particles containing itraconazole coated with at least one surfactant selected from the group consisting of ionic surfactants, non-ionic surfactants, surface-active biological molecules, and amino acids and their derivatives, and wherein the particles have a volume-weighted mean particle size of less than 5 µm as measured by laser diffractometry.

2. The method of claim 1, wherein itraconazole has a solubility in a water-miscible first solvent that is greater than in a second aqueous solvent, and the aqueous suspension is prepared by:

(i) dissolving itraconazole in the first solvent to form a solution;
(ii) mixing the solution with the second solvent to define a pre-suspension; and
(iii) adding energy to the pre-suspension to form particles having an average effective particle size of less than 5 µm, wherein the first or second solvent comprises one or more surfactants selected from the group consisting of nonionic surfactants, ionic surfactants, surface-active biological molecules, and amino acids and their derivatives.

3. The method of claim 1, wherein the ionic surfactant is selected from the group consisting of: anionic surfactants, cationic surfactants, zwitterionic surfactants, and combinations thereof.

4. The method of claim 1, wherein the surfactant is selected from the group consisting of bile salts, polyalkoxyethers, hydroxyethylstarch, polyethylene-660-hydroxystearate, albumin, and phospholipids.

5. The method of claim 1, wherein the aqueous suspension further comprises a pH adjusting agent.

6. The method of claim 1, wherein the aqueous suspension further comprises an osmotic pressure adjusting agent.

7. The method of claim 1, wherein itraconazole is present in the suspension in an amount from about 0.01% to about 50% w/v.

8. The method of claim 1, wherein the surfactant is present in the suspension in an amount from about 0.001% to about 5% w/v.

9. The method of claim 1, wherein the step of administering is by a route selected from the group consisting of parenteral, oral, buccal, periodontal, rectal, nasal, pulmonary, topical, intravenous, intramuscular, intracerebral, subcutaneous, intradermal, intralymphatic, pulmonary, intraarticular, intrathecal, and intraperitoneal.

10. The method of claim 1, wherein itraconazole is present in an amount of from about 0.01% to about 50% w/v, the aqueous suspension comprises an osmotic pressure adjusting agent, and the surfactant is present in an amount of from about 0.001% to about 5% w/v.

* * * * *

UNITED STATES PATENT AND TRADEMARK OFFICE
CERTIFICATE OF CORRECTION

PATENT NO. : 8,263,131 B2
APPLICATION NO. : 12/414484
DATED : September 11, 2012
INVENTOR(S) : Barrett Rabinow et al.

Page 1 of 1

It is certified that error appears in the above-identified patent and that said Letters Patent is hereby corrected as shown below:

On the Cover Page:

At item (75), "Joseph Chung Take Wong" should be -- Joseph Chung Tak Wong --.

Signed and Sealed this
Twenty-second Day of January, 2013

David J. Kappos
*Director of the United States Patent and Trademark Office*